United States Patent
Reed et al.

(10) Patent No.: US 6,265,556 B1
(45) Date of Patent: Jul. 24, 2001

(54) NUCLEIC ACID ENCODING CD40 ASSOCIATED PROTEINS

(75) Inventors: John C. Reed, Carlsbad; Takaaki Sato, San Diego, both of CA (US)

(73) Assignee: The Burnham Institute, La Jolla, CA (US)

(*) Notice: Subject to any disclaimer, the term of this patent is extended or adjusted under 35 U.S.C. 154(b) by 0 days.

(21) Appl. No.: 08/349,357

(22) Filed: Dec. 2, 1994

(51) Int. Cl.$^7$ .................... C07H 21/02; C12N 15/00; C12N 1/20; C12P 21/06

(52) U.S. Cl. .................. 536/23.1; 536/23.5; 435/69.1; 435/70.1; 435/172.1; 435/172.3; 435/320.1

(58) Field of Search .................. 435/69.1, 6, 70.1, 435/172.1, 172.3, 320.1; 536/23.1, 23.5

(56) References Cited

PUBLICATIONS

Armitage et al., "Molecular and biological characterization of a murine ligand for CD40" *Nature* 357:80–82 (1992).
Choi et al., "Inducton of NF–AT in normal B lymphocytes by anti–immunoglobulin or CD40 ligand in conjunction with IL–4." *Immunity* 1:179–187 (1994).
Foy et al., "In vivo CD40–gp39 interactions are essential for thymus–dependent humoral immunity. II. Prolonged suppression of the humoral immune response by an antibody to the ligand for CD40, gp39." *J. Exp. Med.* 178:1567–1575 (1993).
Freemont, P.S. The Ring finger. A novel protein sequence motif related to the Zinc finger. In:Annals New York Academy of Sciences 174–192 (1993).
Gascan et al., "Anti–CD40 monoclonal antibodies of CD4+ T cell clones and IL–4 induce IgG4 and IgE switching in purified human B cells via different signaling pathways." *J. Immunol.* 147:8–13 (1991).
Itoh and Nagata, "A novel protein domain required for apoptosis." *J. Biol. Chem.* 268:10932–10937 (1993).
Itoh et al., "The polpeptide encoded by the cDNA for human cell surface antigen fas can mediate apoptosis." *Cell* 66:233–243 (1991).
Hollenbaugh et al., "The human T cell antigen gp39, a member of the TNF gene family, is a ligand for the C40 receptor: expression of a soluble form of gp39 with B cell co–stimulatory activity." *EMBO J.* 11:4313–4321 (1992).
Kawabe et al., "The immune responses in CD40–deficient mice: impaired immunoglobulin class switching and germinal center formation." *Immunity* 1:167–178 (1994).
Knox and Gordon, "Protein tyrosine phosphorylation is mandatory for CD40–mediated rescue of germinal center B cells from apoptosis." *Eur. J. Immunology* 23:2578–2584 (1993).
Liu et al., "Germinal center cells express bcl–2 protein after activation by signals which prevent their entry into apoptosis." *Eur. J. Immunol.* 21:1905–1910 (1991).

Lovering et al., "Identification and preliminary characterization of a protein motif related to the zinc finger." *Proc. Natl. Acad. Sci. USA* 90:2112–2116 (1993).
Loetscher et al., "Molecular cloning and expression of the human 55 kd tumor necrosis factor receptor." *Cell* 61:351–359 (1990).
Noelle et al., "CD40 and its ligand, an essential ligand–receptor pair for thymus–dependent B–cell activation." *Immunol. Today* 13:431–433 (1992).
Noelle et al., "A39–dKa protein on activated helper T cells binds CD40 and transduces the signal for cognate activation of B cells." *Proc. Natl. Acad. Sci. USA* 89:6550–6554 (1992).
Oehm et al., "Purification and molecular cloning of the APO–1 cell surface antigen, a member of the tumor necrosis factor/nerve growth factor receptor superfamily." *J. Biol. Chem.* 267:10709–10715 (1992).
Paulie et al., "A p50 surface antigen restricted to human urinary bladder carcinomas an B lymphocytes." *Cancer Immunol. Immunother.* 20:23–28 (1985).
Paulie et al., "The human B lymphocyte and carcinoma antigen, CDw40, is a phosphoprotein involved in growth signal transduction," *J. Immunol.* 142:590–595 (1989).
Rabizadeh et al., "Induction of apoptosis by the low–affinity NGF receptor." *Science* 261:345–348 (1993).
Reddy et al., "The cloning and characterization of a maternally expressed novel zinc finger nuclear phosphoprotein (xnf7) in xenopus laevis." *Dev. Biol.* 148:107–116 (1991).
Ren et al., "Signal transduction via CD40 involves activation of lyn kinase and phosphatidylinositol–3–kinase, and phosphorylation of phospholipase C$\gamma$2." *J. Exp. Med.* 179:673–680 (1994).
Rothe et al., "A novel family of putative signal transducers associated with the cytoplasmic domain of the 75 kDa tumor necrosis factor receptor." *Cell* 78:681–692 (1994).
Mosialos, George et al., "The Epstein–Barr Virus Transforming Protein LMP1 Engages Signaling Proteins for the Tumor Necrosis Factor Receptor Family." Cell 80:389–399 (1995).

(List continued on next page.)

*Primary Examiner*—Susan Ungar
(74) *Attorney, Agent, or Firm*—Campbell & Flores LLP

(57) ABSTRACT

The present invention provides a mammalian CD40-associated protein (CAP), a nucleic acid molecule encoding the CAP and antibodies specific for the CAP. The invention further provides a substantially purified human CAP-1 and a nucleic acid molecule encoding human CAP-1. The invention also provides screening assays for identifying an agent that effectively alters the association of a CAP with a second molecule, which can bind to the CAP. In addition, the invention provides methods for identify a CAP agonist or CAP antagonist that can increase or decrease, respectively, the level of expression of the CAP in a cell. Such an effective agent, agonist or antagonist can modulate a function of a cell such as a humoral immune response or cell growth. The invention also provides methods of detecting a CAP in a sample by detecting the CAP or a nucleic acid molecule encoding the CAP. Such methods can be used to diagnose a pathology that is characterized by an increased or decreased level of a CAP in a cell.

19 Claims, 6 Drawing Sheets

PUBLICATIONS

Sato et al., "Interactions among members of the bcl–2 protein family analyzed with a yeast two–hybrid system." *Proc. Natl. Acad. Sci. USA* 91:9238–9242 (1994).

Smith et al., "A receptor for tumor necrosis factor defines an unusual family of cellular and viral proteins." *Science* 248:1019–1023 (1990).

Smith et al., "The TNF receptor superfamily of cellular and viral proteins: activation, costimulation, and death." *Cell* 76:959–962 (1994).

Stamenkovic et al., "A B–lymphocyte activation molecule related to the nerve growth factor receptor and induced by cytokines in carcinomas." *EMBO J.* 8:1403–1410 (1989).

Tagawa et al., "Expression of novel DNA–binding protein with zinc finger structure in various tumor cells." *J. Biol. Chem.* 265:20021–20026 (1990).

Tartaglia et al., "A novel domain within the 55 kd TNF receptor signals cell death." *Cell* 74:845–853 (1993).

Uckun et al., "Stimulation of protein tyrosine phosorylation, phosphoinositide turnover, and multiple previously unidentified serine/threonine–specific protein kinases by the Pan–B–cell receptor CD40/Bp50 at discrete developmental stages of human B–cell ontogeny." *J. Biol. Chem.* 266:17478–17485 (1991).

Cheng, Genhong, et al., "Involvement of CRAF1, a Relative of TRAF, in CD40 Signaling." Science. 267:1494–1498 (1995).

Hu, Hong Ming et al., "A Novel Ring Finger Protein Interacts with the Cytoplasmic Domain of CD40." J. Biol. Chem. 269:30069–30072 (1994).

Sato et al., "A novel member of the TRAF family of putative signal transducing proteins binds to the cytosolic domain of CD40." *FEBS Letters*, 358:113–118 (1995).

```
-136
 -79  GAAACCTGGCTCCTGGCTCCTGGCTCCCTACTCTTCTAAGGATCGCTGTCCTGACAGAAGAGAACTCCTCTTTCCTAAA

1  ATG GAG TCG AAA AAG GAC ATG GAC TCT CCT GGC GCG CTG CAG ACT AAC CCG CCG CTA AAG      60
   1   M   E   S   K   K   D   M   D   S   P   G   A   L   Q   T   N   P   P   L   K       20

61  CTG CAC ACT GAC CGC AGT GCT GGG ACG CCA GTT TTT GTC CCT GAA CAA GGA GGT TAC AAG     120
  21   L   H   T   D   R   S   A   G   T   P   V   F   V   P   E   Q   G   G   Y   K       40

121  GAA AAG TTT GTG AAG ACC GTG GAG GAC AAG TAC AAG TGT CAC AAG TGC CAC CTG GTG CTG     180
  41   E   K   F   V   K   T   V   E   D   K   Y   K   C   H   K   C   H   L   V   L       60

181  TGC AGC CCG AAG CAG ACC GAG TGT GGG CAC CGC TCC TGC GAG AGC ATG GCG GCC CTG         240
  61   C   S   P   K   Q   T   E   C   G   H   R   S   C   E   S   M   A   A   L           80

241  CTG AGC TCT TCA AGT CCA AAA TGT CAA GAG GCG ATT CTG GCT CTT CAG ATC GTT AAA GAT AAG GTG     300
  81   L   S   S   S   P   K   C   Q   E   A   I   L   A   L   Q   I   V   K   D   K   V    100

301  TTT AAG GAT AAT TGC TGC AAG AGA GAA TTA ACG CTG GGA CAT CTG CTG CAT TTA AAA AAT GAT     360
 101   F   K   D   N   C   C   K   R   E   L   T   L   G   H   L   L   H   L   K   N   D    120

361  AGC AGA GGT TGT GCA GAG CAG CTT CCA TGT GTG CGT CCT GAC TGC AAA GAA AAG GTC TTG AGG AAA     420
 121   S   R   G   C   A   E   Q   L   P   C   V   R   P   D   C   K   E   K   V   L   R   K    140

421  TGC CAT TTT GAA GAA CTT CCA TGT CCA GGT TGT TTG CCA TAC CGG GAA GCC ACA TGC AGC CAC TGC     480
 141   C   H   F   E   E   L   P   C   P   G   C   L   P   Y   R   E   A   T   C   S   H   C    160

481  GAC CTG CGA GAC CAC GTG GAG AAG GCG TGT AAA TAC CGG GAA GCC ACA TGC AGC CAC TGC         540
 161   D   L   R   D   H   V   E   K   A   C   K   Y   R   E   A   T   C   S   H   C         180

541  AAG AGT CAG GTT CCG ATG ATC GCG CTG CAG AAA CAC GAA GAC ACC GAC TGT CCC TGC GTG     600
 181   K   S   Q   V   P   M   I   A   L   Q   K   H   E   D   T   D   C   P   C   V        200
```

FIG. IA

```
601 GTG GTG TCC TGC CCT CAC AAG TGC AGC GTC CAG ACT CTC CTG AGG AGC GAG GGG ACA AAC  660
201  V   V   S   C   P   H   K   C   S   V   Q   T   L   L   R   S   E   G   T   N   220

661 CAG CAG ATC AAG GCC CAC GAG GCC AGC TCC GCC GTG CAG CAC GTC AAC CTG CTG AAG GAG  720
221  Q   Q   I   K   A   H   E   A   S   S   A   V   Q   H   V   N   L   L   K   E   240

721 TGG AGC AAC TCG CTC GAA AAG AAG GTT TCC TTG TTG CAG AAT GAA AGT GTA GAA AAA AAC  780
241  W   S   N   S   L   E   K   K   V   S   L   L   Q   N   E   S   V   E   K   N   260

781 AAG AGC ATA CAA AGT TTG CAC AAT CAG ATA TGT AGC TTT GAA ATT GAA AGA CAA  840
261  K   S   I   Q   S   L   H   N   Q   I   C   S   F   E   I   E   R   Q   280

841 AAG GAA ATG CTT CGA AAT AAT GAA TCC AAA ATC CTT CAT TTA CAG CGA GTG ATA GAC AGC  900
281  K   E   M   L   R   N   N   E   S   K   I   L   H   L   Q   R   V   I   D   S   300

901 CAA GCA GAG AAA CTG AAG GAG CTT GAC AAG GAG ATC CGG TCC TTC CGG AAC TGG GAG  960
301  Q   A   E   K   L   K   E   L   D   K   E   I   R   S   F   R   N   W   E   320

961 GAA GCA GAC AAG AGC ATG AAG AGC GCG GGG CAA GTG GCT CGG AAC ACA GGC CTG GAG  1020
321  E   A   D   K   S   M   K   S   A   G   Q   V   A   R   N   T   G   L   E   340

1021 AGC GTG GAC AAG AGC ATG CTG GAG TCC CAG CTG  1080
341  S   V   D   K   S   M   L   E   S   Q   L   360

1081 AGC CGG CAT GAC CAG ATG CTG AGT GTG CAC GAC ATC CGC CTA GCC GAC ATG GAC CTG CGC  1140
361  S   R   H   D   Q   M   L   S   V   H   D   I   R   L   A   D   M   D   L   R   380

1141 TTC CAG GTC CTG GAG ACC GCC AGC TAC AAT GGA GTG CTC ATC TGG AAG ATT CGC GAC TAC  1200
381  F   Q   V   L   E   T   A   S   Y   N   G   V   L   I   W   K   I   R   D   Y   400
```

FIG. 1B

```
1201 AAG CGG CGG AAG CAG GAG GCC GTC ATG GGG AAG ACC CTG TCC CTT TAC AGC CAG CCT TTC  1260
 401  K   R   R   K   Q   E   A   V   M   G   K   T   L   S   L   Y   S   Q   P   F   420

1261 TAC ACT GGT TAC TTT GGC TAT AAG ATG TGT GCC AGG GTC TAC CTG AAC GGG GAC GGG ATG  1320
 421  Y   T   G   Y   F   G   Y   K   M   C   A   R   V   Y   L   N   G   D   G   M   440

1321 GGG AAG GGG ACG CAC TTG TCG CTG TTT TTT GTC ATC ATG CGT GGA GAA TAT GAT GCC CTG  1380
 441  G   K   G   T   H   L   S   L   F   F   V   I   M   R   G   E   Y   D   A   L   460

1381 CTT CCT TGG CCG TTT AAG CAG AAA GTG ACA CTC ATG CTG ATG GAT CAG GGG TCC TCT CGA  1440
 461  L   P   W   P   F   K   Q   K   V   T   L   M   L   M   D   Q   G   S   S   R   480

1441 CGT CAT TTG GGA GAT GCA TTC AAG CCC GAC CCC GTC TTT GTG GCC CAA ACT GTT CTA GAA AAT  1500
 481  R   H   L   G   D   A   F   K   P   D   P   V   F   V   A   Q   T   V   L   E   N   500

1501 GGA GAG ATG AAT ATC GCC TCT GGC TGC CCA GTC TTT ATT AAA GTC ATA GTG GAT ACT TCG GAT CTG  1560
 501  G   E   M   N   I   A   S   G   C   P   V   F   I   K   V   I   V   D   T   S   D   L   520

1561 GGG ACA TAT ATT AAA GAT GAT ACA ATT TTT TTC AAA GAT GAT CCC  1620
 521  G   T   Y   I   K   D   D   T   I   F   F   K   D   D   P   540

1621 CCC GAT CCC TGATAAGTAGCTGGGAGGTGGATTTAGCAGAAGGCAACTCCTCTGGGGATTTGAACCGGTCTGTC  1696
 541  P   D   P                                                                      543

1697 TTCACTGAGGTCCTCGCGCTCAGAAAAGGACCTTGTGAGACGGAGGAAGCGGAGAAGGCGGACGCGTGCCGGCGGGAG  1775
1776 GAGCCACGCGTCGTGAGACCGTGACACCACCTGAGAGAAGCGTTTTATAATAGACTAGCCACACTCTGAAGAATTATTATCCTTCAACA  1854
1855 AGCATAAATATTGCTGTCAGAGAAGGTTTTCATTTTTAAAGATCTAGTTAATTAAGTGAAAACATATATGC  1933
1934 TAAACAAAGAAACATGATTTTTCTTCCTAAACTTGAACACCAAAAACACACACACACACACACGTGGGATAGC  2012
2013 TGGACATGTCAGCATGTTAAGTAAAAGGAGAATTTATGAAATAGTAATGCAATTCTGATATCTTCTTTCTAAAATTCAA  2091
2092 GAGTGCAATTTTG  2104
```

FIG. IC

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 2240 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 137..1766

(xi) SEQUENCE DESCRIPTION: SEQ ID NO:1:

AGAAGTGATG CCACTTGGTT AAGGTCCCAG AGCAGGTCAG AATCAGACCT AGGATCAGAA    60

```
ACCTGGCTCC TGGCTCCTGG CTCCCTACTC TTCTAAGGAT CGCTGTCCTG ACAGAAGAGA        120

ACTCCTCTTT CCTAAA ATG GAG TCG AGT AAA AAG ATG GAC TCT CCT GGC           169
               Met Glu Ser Ser Lys Lys Met Asp Ser Pro Gly
                1               5                  10

GCG CTG CAG ACT AAC CCG CCG CTA AAG CTG CAC ACT GAC CGC AGT GCT         217
Ala Leu Gln Thr Asn Pro Pro Leu Lys Leu His Thr Asp Arg Ser Ala
             15                  20                  25

GGG ACG CCA GTT TTT GTC CCT GAA CAA GGA GGT TAC AAG GAA AAG TTT         265
Gly Thr Pro Val Phe Val Pro Glu Gln Gly Gly Tyr Lys Glu Lys Phe
         30                  35                  40

GTG AAG ACC GTG GAG GAC AAG TAC AAG TGT GAG AAG TGC CAC CTG GTG         313
Val Lys Thr Val Glu Asp Lys Tyr Lys Cys Glu Lys Cys His Leu Val
     45                  50                  55

CTG TGC AGC CCG AAG CAG ACC GAG TGT GGG CAC CGC TCC TGC GAG AGC         361
Leu Cys Ser Pro Lys Gln Thr Glu Cys Gly His Arg Ser Cys Glu Ser
 60                  65                  70                  75

TGC ATG GCG GCC CTG CTG AGC TCT TCA AGT CCA AAA TGT ACA GCG TGT         409
Cys Met Ala Ala Leu Leu Ser Ser Ser Ser Pro Lys Cys Thr Ala Cys
                 80                  85                  90

CAA GAG AGC ATC GTT AAA GAT AAG GTG TTT AAG GAT AAT TGC TGC AAG         457
Gln Glu Ser Ile Val Lys Asp Lys Val Phe Lys Asp Asn Cys Cys Lys
             95                 100                 105

AGA GAA ATT CTG GCT CTT CAG ATC TAT TGT CGG AAT GAA AGC AGA GGT         505
Arg Glu Ile Leu Ala Leu Gln Ile Tyr Cys Arg Asn Glu Ser Arg Gly
        110                 115                 120

TGT GCA GAG CAG TTA ACG CTG GGA CAT CTG CTG GTG CAT TTA AAA AAT         553
Cys Ala Glu Gln Leu Thr Leu Gly His Leu Leu Val His Leu Lys Asn
    125                 130                 135

GAT TGC CAT TTT GAA GAA CTT CCA TGT GTG CGT CCT GAC TGC AAA GAA         601
Asp Cys His Phe Glu Glu Leu Pro Cys Val Arg Pro Asp Cys Lys Glu
140                 145                 150                 155

AAG GTC TTG AGG AAA GAC CTG CGA GAC CAC GTG GAG AAG GCG TGT AAA         649
Lys Val Leu Arg Lys Asp Leu Arg Asp His Val Glu Lys Ala Cys Lys
                160                 165                 170

TAC CGG GAA GCC ACA TGC AGC CAC TGC AAG AGT CAG GTT CCG ATG ATC         697
Tyr Arg Glu Ala Thr Cys Ser His Cys Lys Ser Gln Val Pro Met Ile
            175                 180                 185

GCG CTG CAG AAA CAC GAA GAC ACC GAC TGT CCC TGC GTG GTG GTG TCC         745
Ala Leu Gln Lys His Glu Asp Thr Asp Cys Pro Cys Val Val Val Ser
        190                 195                 200

TGC CCT CAC AAG TGC AGC GTC CAG ACT CTC CTG AGG AGC GAG GGG ACA         793
Cys Pro His Lys Cys Ser Val Gln Thr Leu Leu Arg Ser Glu Gly Thr
    205                 210                 215

AAC CAG CAG ATC AAG GCC CAC GAG GCC AGC TCC GCC GTG CAG CAC GTC         841
Asn Gln Gln Ile Lys Ala His Glu Ala Ser Ser Ala Val Gln His Val
220                 225                 230                 235

AAC CTG CTG AAG GAG TGG AGC AAC TCG CTC GAA AAG AAG GTT TCC TTG         889
Asn Leu Leu Lys Glu Trp Ser Asn Ser Leu Glu Lys Lys Val Ser Leu
                240                 245                 250

TTG CAG AAT GAA AGT GTA GAA AAA AAC AAG AGC ATA CAA AGT TTG CAC         937
Leu Gln Asn Glu Ser Val Glu Lys Asn Lys Ser Ile Gln Ser Leu His
            255                 260                 265

AAT CAG ATA TGT AGC TTT GAA ATT GAA ATT GAG AGA CAA AAG GAA ATG         985
Asn Gln Ile Cys Ser Phe Glu Ile Glu Ile Glu Arg Gln Lys Glu Met
        270                 275                 280

CTT CGA AAT AAT GAA TCC AAA ATC CTT CAT TTA CAG CGA GTG ATA GAC        1033
Leu Arg Asn Asn Glu Ser Lys Ile Leu His Leu Gln Arg Val Ile Asp
    285                 290                 295
```

```
AGC CAA GCA GAG AAA CTG AAG GAG CTT GAC AAG GAG ATC CGG TCC TTC      1081
Ser Gln Ala Glu Lys Leu Lys Glu Leu Asp Lys Glu Ile Arg Ser Phe
300                 305                 310                 315

CGG CAG AAC TGG GAG GAA GCA GAC AGC ATG AAG AGC AGC GTG GAG TCC      1129
Arg Gln Asn Trp Glu Glu Ala Asp Ser Met Lys Ser Ser Val Glu Ser
                320                 325                 330

CTC CAG AAC CGC GTG ACC GAG CTG GAG AGC GTG GAC AAG AGC GCG GGG      1177
Leu Gln Asn Arg Val Thr Glu Leu Glu Ser Val Asp Lys Ser Ala Gly
            335                 340                 345

CAA GTG GCT CGG AAC ACA GGC CTG CTG GAG TCC CAG CTG AGC CGG CAT      1225
Gln Val Ala Arg Asn Thr Gly Leu Leu Glu Ser Gln Leu Ser Arg His
        350                 355                 360

GAC CAG ATG CTG AGT GTG CAC GAC ATC CGC CTA GCC GAC ATG GAC CTG      1273
Asp Gln Met Leu Ser Val His Asp Ile Arg Leu Ala Asp Met Asp Leu
    365                 370                 375

CGC TTC CAG GTC CTG GAG ACC GCC AGC TAC AAT GGA GTG CTC ATC TGG      1321
Arg Phe Gln Val Leu Glu Thr Ala Ser Tyr Asn Gly Val Leu Ile Trp
380                 385                 390                 395

AAG ATT CGC GAC TAC AAG CGG CGG AAG CAG GAG GCC GTC ATG GGG AAG      1369
Lys Ile Arg Asp Tyr Lys Arg Arg Lys Gln Glu Ala Val Met Gly Lys
                400                 405                 410

ACC CTG TCC CTT TAC AGC CAG CCT TTC TAC ACT GGT TAC TTT GGC TAT      1417
Thr Leu Ser Leu Tyr Ser Gln Pro Phe Tyr Thr Gly Tyr Phe Gly Tyr
            415                 420                 425

AAG ATG TGT GCC AGG GTC TAC CTG AAC GGG GAC GGG ATG GGG AAG GGG      1465
Lys Met Cys Ala Arg Val Tyr Leu Asn Gly Asp Gly Met Gly Lys Gly
        430                 435                 440

ACG CAC TTG TCG CTG TTT TTT GTC ATC ATG CGT GGA GAA TAT GAT GCC      1513
Thr His Leu Ser Leu Phe Phe Val Ile Met Arg Gly Glu Tyr Asp Ala
    445                 450                 455

CTG CTT CCT TGG CCG TTT AAG CAG AAA GTG ACA CTC ATG CTG ATG GAT      1561
Leu Leu Pro Trp Pro Phe Lys Gln Lys Val Thr Leu Met Leu Met Asp
460                 465                 470                 475

CAG GGG TCC TCT CGA CGT CAT TTG GGA GAT GCA TTC AAG CCC GAC CCC      1609
Gln Gly Ser Ser Arg Arg His Leu Gly Asp Ala Phe Lys Pro Asp Pro
                480                 485                 490

AAC AGC AGC AGC TTC AAG AAG CCC ACT GGA GAG ATG AAT ATC GCC TCT      1657
Asn Ser Ser Ser Phe Lys Lys Pro Thr Gly Glu Met Asn Ile Ala Ser
            495                 500                 505

GGC TGC CCA GTC TTT GTG GCC CAA ACT GTT CTA GAA AAT GGG ACA TAT      1705
Gly Cys Pro Val Phe Val Ala Gln Thr Val Leu Glu Asn Gly Thr Tyr
        510                 515                 520

ATT AAA GAT GAT ACA ATT TTT ATT AAA GTC ATA GTG GAT ACT TCG GAT      1753
Ile Lys Asp Asp Thr Ile Phe Ile Lys Val Ile Val Asp Thr Ser Asp
    525                 530                 535

CTG CCC GAT CCC T GATAAGTAGC TGGGGAGGTG GATTTAGCAG AAGGCAACTC        1806
Leu Pro Asp Pro
540

CTCTGGGGGA TTTGAACCGG TCTGTCTTCA CTGAGGTCCT CGCGCTCAGA AAAGGACCTT    1866

GTGAGACGGA GGAAGCGGCA GAAGGCGGAC GCGTGCCGGC GGGAGGAGCC ACGCGTGAGA    1926

CACCTGACAC GTTTTATAAT AGACTAGCCA CACTTCACTC TGAAGAATTA TTTATCCTTC    1986

AACAAGCATA AATATTGCTG TCAGAGAAGG TTTTCATTTT CATTTTTAAA GATCTAGTTA    2046

ATTAAGGTGG AAAACATATA TGCTAAACAA AAGAAACATG ATTTTCTTC CTTAAACTTG     2106

AACACCAAAA AACACACACA CACACACACA CGTGGGGATA GCTGGACATG TCAGCATGTT    2166

AAGTAAAAGG AGAATTTATG AAATAGTAAT GCAATTCTGA TATCTTCTTT CTAAAATTCA    2226

AGAGTGCAAT TTTG                                                      2240
```

(2) INFORMATION FOR SEQ ID NO:2:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Ser Ser Lys Lys Met Asp Ser Pro Gly Ala Leu Gln Thr Asn
 1               5                  10                  15

Pro Pro Leu Lys Leu His Thr Asp Arg Ser Ala Gly Thr Pro Val Phe
             20                  25                  30

Val Pro Glu Gln Gly Gly Tyr Lys Glu Lys Phe Val Lys Thr Val Glu
         35                  40                  45

Asp Lys Tyr Lys Cys Glu Lys Cys His Leu Val Leu Cys Ser Pro Lys
 50                  55                  60

Gln Thr Glu Cys Gly His Arg Ser Cys Glu Ser Cys Met Ala Ala Leu
 65                  70                  75                  80

Leu Ser Ser Ser Pro Lys Cys Thr Ala Cys Gln Glu Ser Ile Val
                 85                  90                  95

Lys Asp Lys Val Phe Lys Asp Asn Cys Cys Lys Arg Glu Ile Leu Ala
                100                 105                 110

Leu Gln Ile Tyr Cys Arg Asn Glu Ser Arg Gly Cys Ala Glu Gln Leu
            115                 120                 125

Thr Leu Gly His Leu Leu Val His Leu Lys Asn Asp Cys His Phe Glu
130                 135                 140

Glu Leu Pro Cys Val Arg Pro Asp Cys Lys Glu Lys Val Leu Arg Lys
145                 150                 155                 160

Asp Leu Arg Asp His Val Glu Lys Ala Cys Lys Tyr Arg Glu Ala Thr
                165                 170                 175

Cys Ser His Cys Lys Ser Gln Val Pro Met Ile Ala Leu Gln Lys His
                180                 185                 190

Glu Asp Thr Asp Cys Pro Cys Val Val Val Ser Cys Pro His Lys Cys
            195                 200                 205

Ser Val Gln Thr Leu Leu Arg Ser Glu Gly Thr Asn Gln Gln Ile Lys
210                 215                 220

Ala His Glu Ala Ser Ser Ala Val Gln His Val Asn Leu Leu Lys Glu
225                 230                 235                 240

Trp Ser Asn Ser Leu Glu Lys Lys Val Ser Leu Leu Gln Asn Glu Ser
                245                 250                 255

Val Glu Lys Asn Lys Ser Ile Gln Ser Leu His Asn Gln Ile Cys Ser
                260                 265                 270

Phe Glu Ile Glu Ile Glu Arg Gln Lys Glu Met Leu Arg Asn Asn Glu
            275                 280                 285

Ser Lys Ile Leu His Leu Gln Arg Val Ile Asp Ser Gln Ala Glu Lys
290                 295                 300

Leu Lys Glu Leu Asp Lys Glu Ile Arg Ser Phe Arg Gln Asn Trp Glu
305                 310                 315                 320

Glu Ala Asp Ser Met Lys Ser Ser Val Glu Ser Leu Gln Asn Arg Val
                325                 330                 335

Thr Glu Leu Glu Ser Val Asp Lys Ser Ala Gly Gln Val Ala Arg Asn
            340                 345                 350
```

```
Thr Gly Leu Leu Glu Ser Gln Leu Ser Arg His Asp Gln Met Leu Ser
        355                 360                 365

Val His Asp Ile Arg Leu Ala Asp Met Asp Leu Arg Phe Gln Val Leu
    370                 375                 380

Glu Thr Ala Ser Tyr Asn Gly Val Leu Ile Trp Lys Ile Arg Asp Tyr
385                 390                 395                 400

Lys Arg Arg Lys Gln Glu Ala Val Met Gly Lys Thr Leu Ser Leu Tyr
                405                 410                 415

Ser Gln Pro Phe Tyr Thr Gly Tyr Phe Gly Tyr Lys Met Cys Ala Arg
            420                 425                 430

Val Tyr Leu Asn Gly Asp Gly Met Gly Lys Gly Thr His Leu Ser Leu
        435                 440                 445

Phe Phe Val Ile Met Arg Gly Glu Tyr Asp Ala Leu Leu Pro Trp Pro
    450                 455                 460

Phe Lys Gln Lys Val Thr Leu Met Leu Met Asp Gln Gly Ser Ser Arg
465                 470                 475                 480

Arg His Leu Gly Asp Ala Phe Lys Pro Asp Pro Asn Ser Ser Ser Phe
                485                 490                 495

Lys Lys Pro Thr Gly Glu Met Asn Ile Ala Ser Gly Cys Pro Val Phe
            500                 505                 510

Val Ala Gln Thr Val Leu Glu Asn Gly Thr Tyr Ile Lys Asp Asp Thr
        515                 520                 525

Ile Phe Ile Lys Val Ile Val Asp Thr Ser Asp Leu Pro Asp Pro
    530                 535                 540
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:3:

GGAATTCAAA AAGGTGGCCA AG                                      22

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

TGATCATCAC TGTCTCTCCT GCAC                                24

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:5:

GGAATTCAAG GCCCCCCACC CCAAG                               25

(2) INFORMATION FOR SEQ ID NO:6:

(i) SEQUENCE CHARACTERISTICS:

(A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

TGATCAACTC TCTTTGCCAT CCTC                                              24

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:7:

GGAATTCAAG AGAAAGGAAG TACAG                                             25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:8:

GTGATCACTA GACCAAGCTT TGGAT                                             25

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:9:

GGAATTCAAA AGAAGCCCT TGTGCCT                                            27

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:10:

GGTCGACTTA ACTGGGCTTC ATCCCA                                            26

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

GGGATCCGCT ACCAACGGTG GAAG                                              24

(2) INFORMATION FOR SEQ ID NO:12:

(i) SEQUENCE CHARACTERISTICS:
        (A) LENGTH: 25 base pairs (B) TYPE: nucleic acid
        (C) STRANDEDNESS: single
        (D) TOPOLOGY: linear (xi) SEQUENCE DESCRIPTION: SEQ ID NO:12:

GGTCGACTCA TCTGAGAAGA CTGGG                                                   25

(2) INFORMATION FOR SEQ ID NO:13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:13:

TAATACGACT CACTATAGGG AGACCACATG GATGATGTAT ATAACTATCA TTTC                   54

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:14:

CTACCAGAAT TCGGCATGCC GGTAGAGGTG TGGTCA                                       36

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

GCGTTAACTG CTCTGCACAA                                                         20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

GTACATTTTG GACTTGAAGA                                                         20

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:17:

GAATTCCCGG GGATCCGTCG ACCTGCAG                                                28

NUCLEIC ACID ENCODING CD40 ASSOCIATED PROTEINS

FIELD OF THE INVENTION

This invention relates generally to the fields of molecular biology and molecular medicine and more specifically to proteins involved in the regulation of immunological responses and cell growth

BACKGROUND INFORMATION

Immunological responses can be broadly classified as humoral and cell-mediated. Humoral responses are mediated by antibody molecules present in plasma, lymph or tissue fluids and produced by plasma cells that differentiate from immature B cells. An antibody has both recognition and effector function that plays a key role in eliminating bacteria, neutralizing viruses and in triggering degranulation of mast cells and basophils. Cell-mediated immune responses are those mediated by antigen-specific T cells and various nonspecific cells of the immune system, such as natural killer cells, phagocytic cells and other white blood cells. Cell-mediated responses protect against infections due to intracellular bacteria, viruses or yeasts.

Despite the separate classifications of immunological responses, the humoral immune response is highly dependent for its function on a class of T cells known as T helper cells ($T_H$ cells). Antigens that require $T_H$ cells to elicit a humoral immune response are known as T-dependent antigens. During the humoral response to T-dependent antigens, $T_H$ cells make direct contact with B cells, which results in B cell proliferation and immunoglobulin (Ig) class switching from the IgM class to IgG, IgA or IgE antibody classes. Various receptor-ligand interactions are involved in mediating contact between a $T_H$ cell and a B cell during the response to a T-dependent antigen. In particular, CD40—CD40 ligand (CD40L) pairing is critical to achieving this cell-cell interaction.

CD40L and CD40 are both transmembrane glycoproteins that are homologous to tumor necrosis factor (TNF) and TNF receptors, (TNF-R), respectively. CD40 has a role in a variety of B cell functions, such as inducing Ig class-switching, acting as a cofactor with specific antigen and certain lymphokines for B cell mitogenesis, providing signals that prevent apoptotic cell death and triggering B cell adhesion to other cells. CD40L is not expressed on resting $T_H$ cells but can be induced after the cell contacts specific antigen.

The function of CD40/CD40L interactions in the immune response is revealed by hereditary abnormalities of CD40L, which cause an X-linked immunodeficiency syndrome. This syndrome is characterized by hyper-production of IgM, reduced levels of IgG, failure to produce IgA and IgE and absence of germinal centers in lymphoid tissues. The germinal centers are structures associated with T-dependent antibody responses. Nearly identical abnormalities are seen in transgenic mice that do not express CD40. These results indicate that the CD40/CD40L interaction provides a non-redundant pathway required for achieving T-dependent antibody responses in vivo.

It currently is unclear how CD40 transduces its CD40L-binding signal into a B cell. Since CD40 is present on the cell surface, its action likely is mediated by CD40 binding to one or more intracellular proteins, which ultimately effect signal transduction pathways that control Ig class-switching, cell proliferation and cell survival. However, the cytoplasmic domain of CD40 provides no clues as to how intracellular signalling is accomplished since the domain lacks homology to kinases or other enzymes known for mediating intracellular signalling.

The identification of intracellular proteins that can associate with CD40 and transduce the CD40L-binding signal into a cell would provide a means to manipulate various cellular functions, including, for example, humoral immune responses and apoptosis. Thus, a need exists to identify proteins that associate with CD40. The present invention satisfies this need and provides additional advantages as well.

SUMMARY OF THE INVENTION

The present invention provides substantially purified mammalian CD40-associated protein (CAP), which is related to the TRAF family of signal transducing proteins. The invention also provides nucleic acid molecules encoding CAPs, vectors containing the nucleic acid molecules and host cells containing the vectors. For example, the invention provides a substantially purified human CAP-1 and a nucleic acid molecule encoding human CAP-1. The invention also provides antibodies that can specifically bind to a CAP.

The present invention also provides a screening assay useful for identifying agents that can effectively alter the association of a CAP with a second molecule that binds to the CAP in a cell. By altering the association of a CAP with a second molecule, an effective agent can increase or decrease the level of apoptosis in a cell.

The invention further provides methods of identifying a CAP agonist or CAP antagonist that can increase or decrease, respectively, the level of expression of the CAP in a cell and thereby modulate a function of the cell.

The invention also provides methods of detecting a CAP in a sample by detecting the presence of the CAP protein or of a nucleic acid molecule encoding the CAP. Such methods can be used to diagnose a pathology that is characterized by an increased or decreased level of expression of a CAP in a cell.

BRIEF DESCRIPTION OF THE FIGURES

FIG. 1 lists the complete nucleotide sequence (SEQ ID NO: 1) and the deduced amino acid sequence (SEQ ID NO: 2) of CAP-1. Single letter amino acid symbols are used.

Figure 2:
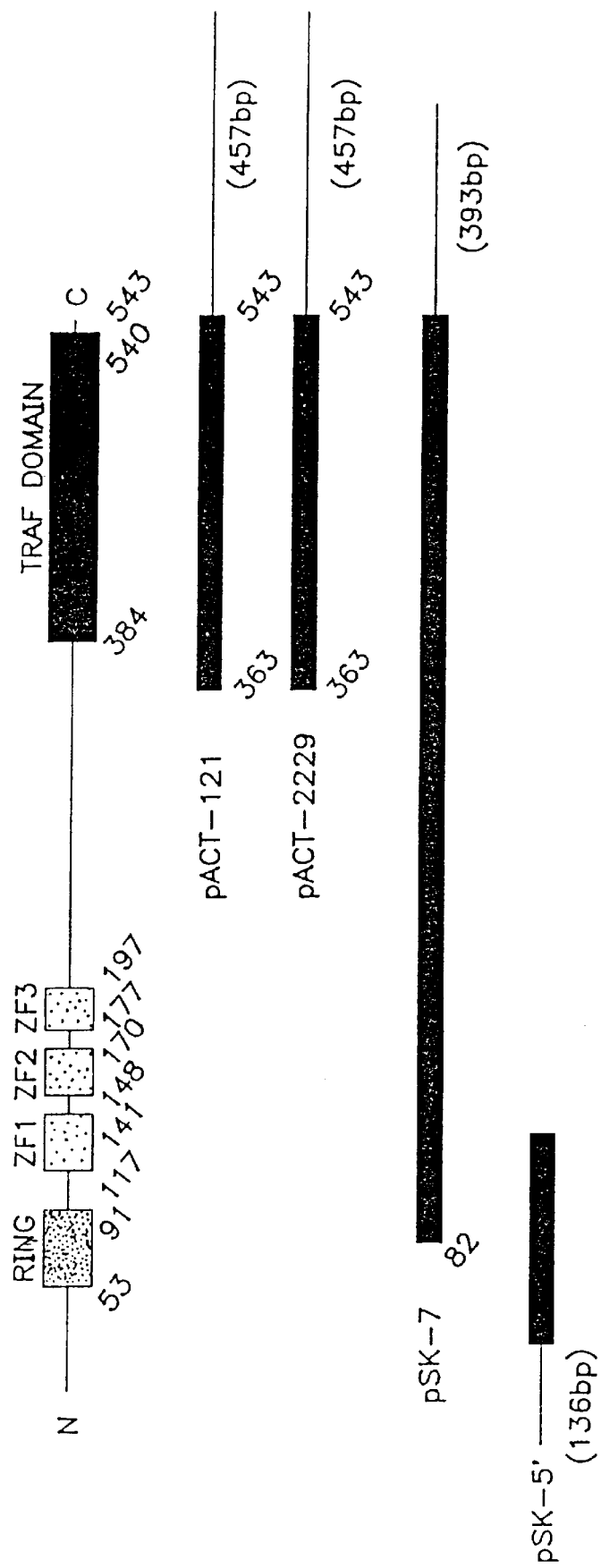
FIG. 2 schematically shows the amino sequence of CAP-1 and depicts the relative locations of the RING finger domains, zinc finger domains and the TRAF domain. Numbers indicate the amino acid position beginning from the N-terminus and ending at the C-terminus. Below the diagram are shown the regions of CAP-1 contributed by three separate cDNA sequences.

Cloning was performed so as to maintain the open reading frame of LexA into the inserted sequence such that a LexA/CD40 fusion protein was produced.

DETAILED DESCRIPTION OF THE INVENTION

The present invention provides a novel CD40-associated protein (CAP), designated CAP-1. As used herein, the term "CD40-associated protein" or "CAP" means a protein that binds specifically to CD40, which is a cell surface receptor involved in apoptosis. A CAP can be identified, for example, using the assays described in Examples I and II.

Although the term "CAP" is used generally, it should be recognized that a CAP identified using an assay described herein can be a portion of a protein, which is considered to be a candidate CAP. As used herein, the term "candidate CAP" refers to a protein that corresponds to a peptide or polypeptide sequence that can bind CD40 but that consists of only a portion of the full length protein. For example, a CAP such as CAP-1 can be identified by obtaining cDNA sequences from a cDNA library, expressing the polypeptides encoded by the cDNA sequences and detecting polypeptides that can bind CD40. Although such polypeptides are considered CAP's, it is well known that a cDNA sequence obtained from a cDNA library may not encode the full length protein. For example, a cDNA can encode a polypeptide such as the CAP-1 cytoplasmic domain that is only a portion of the full length CAP-1 protein but, nevertheless, assumes an appropriate conformation so as to bind CD40. It is recognized, however, that in the full length protein, the polypeptide sequence can assume a conformation that does not bind CD40 due, for example, to steric blocking of the CD40 binding site. Such a full length protein is an example of a candidate CAP. For convenience of discussion, the term "CAP" as used herein is intended to include a candidate CAP. Thus, a CAP can be a protein or a polypeptide portion of a protein that binds CD40.

Since CD40 is critical for T cell-dependent antibody responses, the association of a CAP with CD40 can affect the humoral immune response by modulating the level of production of IgG, IgA and IgE. CD40 is a ~50 kiloDalton (kDa) glycoprotein receptor that is expressed on the surface of B cells, some activated T cells, monocytes, follicular dendritic cells, basal epithelial cells as well as some epithelial and non-epithelial carcinomas (Paulie et al., Immunotherapy 20:23–28 (1985); Paulie et al., J. Immunol. 142:590–595 (1989); Clark and Ledbetter, Proc. Natl. Acad. Sci., USA 83:4494–4498 (1986); Ledbetter et al., J. Immunol. 138:788–794 (1987); Young et al., Int. J. Canc. 43:786–794 (1989)). The function of CD40 has been studied extensively in B cells, where it is believed to play an important role in regulation of cell proliferation, apoptosis, Ig class-switching, generation of memory B cells, modulation of cytokine gene expression and cell adhesion (Clark and Ledbetter, Nature 367:425–428 (1994); Noelle et al., Today 13:431–433 (1992a); Lederman et al., Curr. Opin. Immunol. 5:439–444 (1993)). For example, CD40 can act as a cofactor in combination with anti-Immunoglobulin M (IgM) antibodies, anti-CD20 antibodies, phorbol myristic acetate or interleukin-4 (IL-4) to stimulate proliferation of resting primary B cells (Clark & Ledbetter, supra, 1986); Gordon et al., Eur. J. Immunol. 17:1535–1538 (1987)).

CD40 also provides signals that rescue germinal center B cells from apoptotic cell death and that induce production of the apoptosis-blocking oncoprotein Bcl-2, suggesting a role for CD40 in the generation of long-lived memory B cells (Liu et al., Nature 342:929–931 (1989); Liu et al., Eur. J. Immunol. 21:1905–1910 (1991)). In addition, CD40 synergizes with IL-4 to induce IgE synthesis (Jabara et al., J. Exp. Med. 172:1861–1864 (1990); Gascan et al., J. Immunol. 147:8–13 (1991)) and cooperates with IL-10 or TGF-β to stimulate IgA production (DeFrance et al., Amer. J. Exp. Med. 175:671–682 (1992)). Chimeric proteins that contain the CD40 extracellular domain fused to the Fc portion of IgG, function as competitive antagonists of CD40 and can block B cell proliferation induced by activated T cells and inhibit Ig production stimulated by activated T cells and IL-4 or IL-5 (Noelle et al., Proc. Natl. Acad. Sci., USA 89:6550–6554 (1992b)).

The ligand for CD40 (CD40L) is expressed on the surface of activated helper T cells, as well as mast cells and basophils as a type II transmembrane glycoprotein (Armitage et al., Nature 357:80–82 (1992); Hollenbaugh et al., EMBO J. 11:4313–4321 (1992); Gauchet et al., Nature 365:340–343 (1993)). CD40L thus triggers CD40 action through a mechanism involving cell-cell contact. The importance of the CD40/CD40L interaction for the regulation of T cell-dependent humoral immune responses was demonstrated by experiments in which antibodies to CD40L inhibited the generation of primary and secondary humoral immune responses (Foy et al., J. Exp. Med. 178:1567–1575 (1993)).

Alteration in CD40/CD40L interactions are involved in human diseases. Mutations in the CD40L in humans causes an X-linked immunodeficiency syndrome characterized by excess production of IgM and by an absence of production of IgG, IgA and IgE due to a failure of B cells to undergo Ig class-switching (Allen et al., Science 259:990–993 (1993); DiSanto et al., Nature 361:541–543 (1993); Korthauer et al., Nature 361:539–543 (1993); Fuleihan et al., Proc. Natl. Acad. Sci., USA 90:2170–2173 (1993)). Thus, CD40L/CD40 interactions can be involved in Ig class-switching in vivo. Patients with hyper-IgM syndrome have normal numbers of T cells and B cells and intact cellular immune responses, but often develop lymph node hyperplasia and fail to form germinal centers (Clark and Ledbetter, supra, 1994). Likewise, transgenic mice with homozygous disruptions of their CD40 genes fail to form germinal centers and do not produce IgG, IgA and IgE responses to T cell-dependent antigens, but can mount normal IgM and IgG responses to T cell-independent antigens (Kawabe et al., Immunity 1:167–178 (1994)). Antibodies to CD40L prevent collagen-induced arthritis in an animal model (Durie et al., Science 261:1328–1330 (1993)), suggesting that inhibition of CD40-triggering could provide a means of therapeutically intervening in some autoimmune diseases. CD40L is expressed on mast cells and basophils, which play a key role in mediating atopic diseases. Since such cells induce production of IgE synthesis by B cells co-stimulated with IL-4, the CD40/CD40L based interaction between B cells and either basophils or mast cells represents a critical point for controlling IgE-mediated atopic diseases (Gauchat et al., Nature 365:340–343 (1993).

CD40 and CD40L are members of the tumor necrosis factor receptor (TNF-R) family and TNF family, respectively. The TNF-R family includes the p50/55 TNF-R1, p75/80 TNF-R2, p75 nerve growth factor (NGF) receptor, CD27, CD30 and Fas (Smith et al., Cell 76:959–962 (1994)). The ligands for these receptors are trimeric protein complexes that presumably trigger their respective receptors by inducing receptor chain clustering. Molecular cloning of cDNA sequences for CD40 indicates that the extracellular domain of this receptor contains several cysteine residues, whose positions are conserved among all members of this receptor family, and four copies of a repeated domain structure found in TNF-like receptors. Among the various members of the TNF-R family, CD40 is most similar to p75 NGF-R (Stamenkovic et al., *EMBO J.* 8:1403–35 1410 (1989)).

The predicted cytoplasmic domain of CD40 contains 62 amino acids. The cytoplasmic domain bears no resemblance to kinases or other enzymes that might suggest a mechanism for signal transduction by this protein. However, a region within the cytoplasmic domain of CD40 shares a limited degree of homology to a conserved domain found in the cytosolic tails of p75 NGF-R (22%), TNF-R1(31%) and Fas (41%). In TNF-R1 and Fas, this conserved domain is required for transducing a signal that results in cell death, suggesting that this structure either is involved in receptor aggregation after ligand binding or represents a site that is required directly or indirectly for binding of signal transducing intracellular proteins to these receptors (Itoh et al., *J. Biol. Chem.* 268:10932–10937 (1993); Oehm et al., *J. Biol. Chem.* 267:10709–10715 (1992); Tartaglia et al., *Cell* 74:845–853 (1993)). Although CD40 and p75 NGF-R generate signals that suppress apoptosis, they also accelerate apoptosis when ectopically expressed in certain neural cell lines in the absence of ligands (Rabizadeh et al., *Science* 261:345–348 (1993)). In such neural cells, CD40 and p75 NGF-R also can delay cell death relative to untransfected cells when triggered with appropriate ligands. Thus, under some circumstances, CD40 and NGF-R, like TNF-R and Fas, can regulate signal transduction pathways leading to cell death.

Although the effects of CD40 on the regulation of apoptosis require the presence of the cytosolic domain, the biochemical mechanism of action remains unknown. In this regard, antibody-mediated crosslinking of CD40 on the surface of B cells can induce turnover of phosphoinositides and phosphorylation of phosphatidyl-inositol-3'-kinase (PI3K), phospholipase-C-γ, and several unknown intracellular proteins, and can increase the activities of the protein tyrosine kinase Lyn and of PI3K (Uckun et al., *J. Biol. Chem.* 266:17478–17485 (1991); Gordon et al., *J. Immunol.* 140:1425–1430 (1988); Ren et al., *J. Exp. Med.* 179:673–680 (1994)). In combination with IL-4, CD40 also can activate the transcription factor NF-AT (Choi et al., *Immunity* 1:179–187 (1994)). However, it is unclear how these biochemical events are regulated by CD40 and what their relevance is to the biological effects of CD40 on B cells and other types of cells.

The identification herein of CAP-1 provides a means to manipulate the signal transduction pathways controlled by CD40 and allows for the development of assays that are useful for identifying agents that effectively alter the association of CAP-1 with CD40. Such agents can be useful, for example, for effectively treating cancer in a subject or for treating an autoimmune disease, immunodeficiency disease or neurodegenerative disease.

A CAP such as CAP-1 can be identified by detecting the association of the CAP with CD40. Such an association can be identified using an in vivo assay such as a yeast two hybrid assay (see Example I) or an in vitro assay (see Example II). As used herein, the term "associate" or "association" means that a CAP and CD40 can bind to each other relatively specifically and, therefore, can form a bound complex. In particular, the association of a CAP, such as CAP-1, and CD40 is sufficiently specific such that the bound complex can form in vivo in a cell or in vitro under suitable conditions (see Example II). Other methods for determining whether a protein can bind CD40 and, therefore, is a CAP are known in the art and include, for example, equilibrium dialysis.

In a normal cell, a steady state level of association of CAP-1 with CD40 can affect the normal level of apoptosis in that cell type. An increase or decrease in the steady state level of association of CAP-1 with CD40 in a cell can result in an increased or decreased level of apoptosis in the cell, which can result in a pathology in a subject.

The normal association of CAP-1 with CD40 in a cell can be altered due, for example, to the expression in the cell of a variant CAP-1 or a variant CD40, either of which can compete for binding with CAP-1 that normally binds to CD40 in the cell. In this case, the association of CAP-1 with CD40 can be decreased in a cell. The term "variant" is used generally herein to mean a protein such as CAP-1 or CD40 that is different from the protein normally found in a particular cell type. The normal association of CAP-1 with CD40 in a cell also can be increased or decreased due, for example, to contact of the cell with an agent such as a drug that can effectively alter the association of CAP-1 with CD40 in a cell.

CAP-1 was identified using the yeast two hybrid system (Fields and Song, *Nature* 340:245–246 (1989); Vojtek et al., *Cell* 74:205–214 (1993); Durfee et al., *Genes Devel.* 7:555–569 (1993), each of which is incorporated herein by reference). An in vivo transcription activation assay such as the yeast two hybrid system is particularly useful for identifying and manipulating the association of proteins. The results observed using such an assay likely mirror the interactions that naturally occur in a cell. Thus, the results obtained in such an in vivo assay can be predictive of results that can occur in a cell in a subject such as a human subject.

A transcription activation assay such as the yeast two hybrid system is based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two proteins. The DNA-binding domain and trans-activation domain can be bridged, for example, by expressing the DNA-binding domain and trans-activation domain as fusion proteins (hybrids), provided that the proteins that are fused to the domains can associate with each other. The non-covalent bridging of the two hybrids brings the DNA-binding and trans-activation domains together and creates a transcriptionally competent complex. The association of the proteins is determined by observing transcriptional activation of a reporter gene (see Example I).

The yeast two hybrid system exemplified herein uses various strains of S. cerevisiae as host cells for vectors that express the hybrid proteins. A transcription activation assay also can be performed using, for example, mammalian cells. However, the yeast two hybrid system is particularly useful due to the ease of working with yeast and the speed with which the assay can be performed. For example, yeast host cells containing a lacZ reporter gene linked to a LexA operator sequence were used to demonstrate that CAP-1 can interact with CD40 (Example I). The DNA-binding domain consisted of the LexA DNA-binding domain, which binds the LexA promoter, fused to a portion of CD40 and the trans-activation domain consisted of a GAL4 trans-activation domain fused to cDNA sequences, some of which encoded a CAP. When the LexA domain was non-covalently bridged to a trans-activation domain fused to a CAP, the association of CD40 and CAP-1 was identified by activated transcription of the reporter gene.

A CAP also can be identified using an in vitro assay such as an assay utilizing, for example, a glutathione-S-transferase (GST) fusion protein as described in Example II. Such an in vitro assay provides a simple, rapid and inexpensive method for identifying and isolating a CAP. Such an in vitro assay is particularly useful for confirming results obtained in vivo and can be used to characterize specific binding domains of a CAP (see Example II). For example, a GST/CD40 fusion protein can be expressed and can be purified by binding to an affinity matrix containing immobilized glutathione. If desired, a sample that can contain a CAP or an active fragment of a CAP can be passed over an affinity column containing bound GST/CD40 and a CAP that binds to CD40 can be obtained. GST/CD40 also can be used to screen a cDNA expression library, wherein binding of the CD40 fusion protein to a clone indicates that the clone contains a cDNA encoding a CAP. In addition to it's use in detecting and purifying a CAP, the in vitro assay provides a useful method to screen for a small molecule inhibitor of a particular CAP-CD40 interaction.

Figure 3:
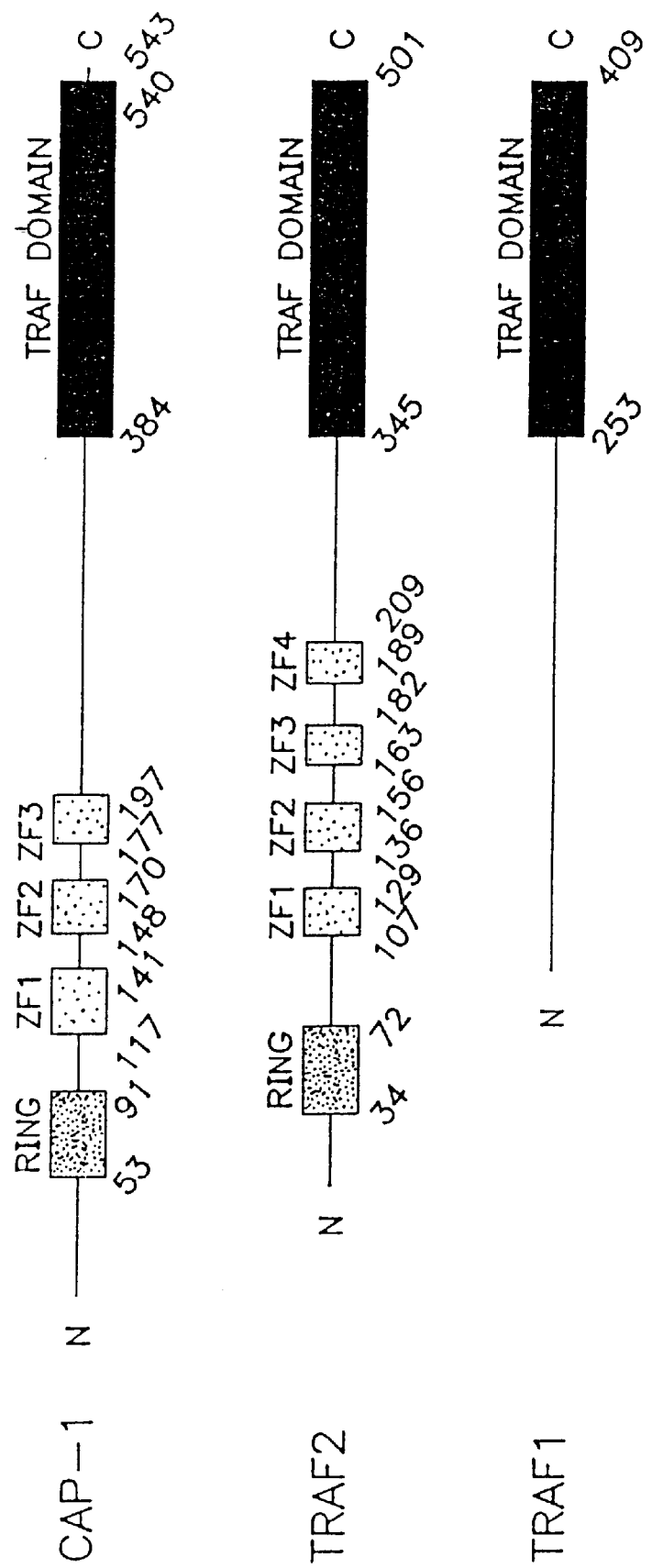
FIG. 3 schematically compares the structures of TRAF-domain family of proteins CAP-1, TRAF1 and TRAF2. The positions of RING finger, zinc finger and TRAF domains are indicated. Numbers indicate the positions of amino acids beginning at the N-terminus.

Using these in vitro and in vivo assays, CAP-1 was demonstrated to associate with CD40. CAP-1 contains a C-terminal domain with strong amino acid sequence homology to a conserved region that is present in two putative signal transducing proteins that bind to the cytosolic domain of p75/80 TNF-R2. These proteins have been designated TNF-R2 associated factors-1 and -2 (TRAF1 and TRAF2) (Rothe et al., *Cell* 78:681–692 (1994)). The TRAF domain in CAP-1 can mediate the interactions of CAP-1 with CD40 and allows for homodimerization of CAP-1 proteins. Like the TRAF2 protein, CAP-1 also contains a RING finger motif and zinc finger-like domains, similar to those found in several regulatory proteins that can interact with DNA or RNA (see FIG. 3 and Example III). CAP-1 thus represents a novel member of a family of proteins that can interact with the cytoplasmic domains present in the TNF-R family proteins and can be involved in signal transduction in a cell.

The present invention provides a substantially purified mammalian CAP or an active fragment thereof, which can bind CD40. In addition, the invention provides human CAP-1 having substantially the amino acid sequence shown in FIG. 1 (SEQ ID NO: 2). The amino acid sequence of human CAP-1 was derived from the nucleotide sequence shown in FIG. 1 (SEQ ID NO: 1).

As used herein, the term "substantially the amino acid sequence" means the disclosed amino acid sequence for human CAP-1 (SEQ ID NO: 2) as well as amino acid sequences that are similar to SEQ ID NO: 2, but have one or more amino acid additions, deletions or substitutions that do not substantially alter the ability of the encoded protein to function like CAP-1 and bind to CD40 or to another protein such as a member of the TRAF family of proteins. As used herein, the term "substantially purified" means a protein that is in a form that is relatively free from contaminating lipids, proteins, nucleic acids or other cellular material normally associated with a protein in a cell. A substantially purified human CAP-1 protein can be obtained, for example, using well known biochemical methods of purification or by expressing a recombinant nucleic acid molecule encoding CAP-1 such as the nucleic acid molecule shown as SEQ ID NO: 1. In addition, an amino acid sequence consisting of at least a portion of the amino acid sequence of SEQ ID NO: 2 can be chemically synthesized or can be produced by expressing a portion of the nucleotide sequence shown as SEQ ID NO: 1.

As used herein, the terms "protein" or "polypeptide" are used in the broadest sense to mean a sequence of amino acids that can be encoded by a cellular gene or by a recombinant nucleic acid sequence or can be chemically synthesized. In some cases, the term "polypeptide" is used in referring to a portion of an amino acid sequence encoding a full length protein. An active fragment of CAP-1 as defined below can be an example of such a polypeptide. A protein can be a complete, full length gene product, which can be a core protein having no amino acid modifications or can be a post-translationally modified form of a protein such as a phosphoprotein, glycoprotein, proteoglycan, lipoprotein or nucleoprotein.

A CAP such as a CAP-1, can be characterized by its ability to associate with CD40. As used herein, the term "CD40" means the full length CD40 protein or a portion of the full length CD40 protein such as the CD40 (positions 220–271) or CD40 (positions 225–269) portions of CD40, either of which can associate with CAP-1 (see Example II). It should be recognized that the ability of a CAP to associate with CD40 can be due to a portion of the full length CAP as is demonstrated herein using a portion of CAP-1.

As used herein, the term "active fragment" means a CAP that is a portion of a full length protein, provided that the portion has an activity that is characteristic of the corresponding full length protein. For example, an active fragment of CAP-1, such as the cytoplasmic domain can have an activity such as the ability, for example, to bind CD40 or to mediate signal transduction after binding to CD40 or to elicit an immune response. The characteristic of an active fragment of a CAP to elicit an immune response is useful for obtaining an anti-CAP antibody. Thus, the invention also provides active fragments of a CAP, which can be identified using the assays described below.

The full length CAP-1 protein contains 543 amino acids and has an estimated molecular mass of 62 kDa. The cytosolic region of CAP-1 binds to a 45 amino acid cytosolic domain of CD40 (positions 225 to 269) that is weakly homologous (22 to 41%) to domains found in the cytosolic portions of TNF-R1, Fas, and p75 NGF-R. This cytosolic domain is required for TNF-R1-mediated and Fas-mediated cytotoxicity (Itoh et al., *Cell* 66:233–243 (1993); Tartaglia et al., *Cell* 74:845–853 (1993)).

The cytoplasmic TRAF domain of CAP-1 can bind to CD40 and can form dimers as disclosed herein (see Examples I and II). The TRAF1 and TRAF2 proteins can form homotypic and heterotypic dimers (Rothe et al., supra, 1994), suggesting their TRAF domains mediate dimer formation in a manner similar to the TRAF domain of CAP-1. In view of the structural similarities between the TRAF domains of TRAF1, TRAF2 and CAP-1, it is likely that all three proteins can form dimers with each other in a cell. Heterodimer formation between TRAF family members can provide an additional degree of specificity for regulating signal transduction in different cell types.

CAP-1 contains several sequences that are homologous to domains commonly found in DNA binding proteins. These sites include a RING finger domain (see Freemont, *Ann. New York Acad. Sci.* 174–172 (1993); Schwabe and Klug, *Struct. Biol.* 1:345–349 (1994); Barlow et al., *J. Mol. Biol.* 237:201–211 (1994)) and three zinc finger domains. TRAF2 is similar to CAP-1 in having a single RING finger domain and in having multiple zinc finger domains, while TRAF1 lacks these domains (see FIGS. 2 and 3). The presence of DNA binding motifs in CAP-1 and TRAF2 indicates these proteins can have a role in the regulation of gene transcription.

The present invention provides a reagent that specifically binds to a CAP. As used herein the term "reagent" means a chemical or biological molecule that can specifically bind to a CAP. Examples of a reagent include CD40, an anti-CAP antibody or a protein containing a TRAF domain. As used herein, the term "antibody" is used in its broadest sense to include polyclonal and monoclonal antibodies, as well as polypeptide fragments of antibodies that retain a specific binding activity for a specific antigen of at least about $1 \times 10^5$ $M^{-1}$. One skilled in the art would know that anti-CAP antibody fragments such as Fab, F(ab')$_2$, Fv and Fd fragments can retain specific binding activity for a CAP and, thus, are included within the definition of an antibody. In addition, the term "antibody" as used herein includes naturally occurring antibodies as well as non-naturally occurring antibodies and fragments of antibodies that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

An anti-CAP antibody can be prepared using well known methods as described, for example, by Harlow and Lane, *Antibodies: A laboratory manual* (Cold Spring Harbor Laboratory Press, 1988), which is incorporated herein by reference. For example, CAP-1 protein or a portion of the CAP-1 protein can be used as an immunogen. Such an immunogen can be prepared from natural sources or produced recombinantly or, in the case of a portion of the protein, can be chemically synthesized. Non-immunogenic peptides of a CAP protein can be made immunogenic by coupling to a carrier molecule such as bovine serum albumin (BSA) or keyhole limpet hemocyanin (KLE) as described, for example, by Harlow and Lane (supra, 1988). In addition, a CAP fusion protein can be expressed as described in Example II and can be purified and used as an immunogen to obtain anti-CAP-1 antibodies.

Polyclonal antibodies can be raised, for example, in rabbits. In addition, monoclonal antibodies can be obtained using well known methods (see, for example, Reed et al., *Anal. Biochem.* 205:70–76 (1992), which is incorporated herein by reference; see, also, Harlow and Lane, supra, 1988). For example, spleen cells from a CAP-1 immunized mouse can be fused to an appropriate myeloma cell line such as SP2/0 or P3x653.Ag8 myeloma cells to produce hybridoma cells. Cloned hybridoma cell lines can be screened using a labelled CAP-1 immunogen to identify clones that secrete monoclonal antibodies. Hybridomas that express antibodies having a desirable specificity and affinity can be isolated and utilized as a continuous source of antibodies. One skilled in the art would know that a dependable source of monoclonal antibodies is desirable, for example, for preparing diagnostic kits as described below.

The invention also provides a substantially purified nucleic acid molecule encoding a CAP. For example, the invention provides a substantially purified nucleic acid molecule having substantially the nucleotide sequence encoding human CAP-1 shown in FIG. 1 (SEQ ID NO: 1). Although the disclosed cDNA sequence lacks a polyadenylation site, it contains the complete open reading frame encoding human CAP-1.

As used herein, the term "substantially purified" means a nucleic acid molecule that is in a form that is relatively free from contaminating lipids, proteins, nucleic acids or other cellular material normally associated with a nucleic acid molecule in a cell. A substantially purified nucleic acid molecule can be obtained, for example, by recombinant DNA methods as described herein (see, also, Sambrook et al., *Molecular Cloning: A laboratory manual* (Cold Spring Harbor Laboratory Press 1989), which is incorporated herein by reference) or can be chemically synthesized.

As used herein, the term "substantially the nucleotide sequence" means the disclosed nucleotide sequence for human CAP-1 (SEQ ID NO: 1), as well as a similar sequence that contains, for example, different nucleotides than shown in SEQ ID NO: 2, but that, as a result of the degeneracy of the genetic code, encodes the same amino acid sequence as shown in SEQ ID NO: 2. In addition, a nucleic acid molecule of the invention can encode a portion of CAP-1 or can encode a CAP-1 having substantially the amino acid sequence shown in FIG. 1 (SEQ ID NO: 2).

The invention also provides a nucleotide sequence that can hybridize to a portion of a nucleic acid molecule encoding a mammalian CAP under relatively stringent hybridization conditions. Such a nucleotide sequence should be at least ten nucleotides in length and can be prepared, for example, by restriction endonuclease digestion of a cloned nucleic acid molecule encoding a CAP, such as CAP-1, or by PCR amplification of a portion of the nucleic acid molecule shown in FIG. 1 (SEQ ID NO: 1), or by chemical synthesis. Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence. If desired, a hybridizing nucleotide sequence can be detectably labelled and used as a probe or can be used as a primer for PCR. Methods for detectably labelling a nucleotide sequence are well known in the art (see, for example, Sambrook et al., supra, 1989; see, also, Ausubel et al., *Current Protocols in Molecular Biology vol. 2*, chapter 10 (Greene Publ., NY 1989), which is incorporated herein by reference).

A CAP also can be a mutant CAP, which is a CAP that contains at least one or a few amino acid additions, deletions or substitutions that result in the loss of an activity of the CAP but that do not significantly alter the ability of the mutant CAP to bind CD40 or a protein having a TRAF domain. For example, a mutant CAP can lose the ability to mediate signal transduction following binding to CD40. Such a mutant CAP can modulate an immune response, for example, by binding to CD40, thereby preventing binding of a wild type CAP to CD40 in a cell. As used herein, the term "modulate" means increase or decrease. A mutant CAP can be obtained, for example, by site directed mutagenesis or codon based mutagenesis of a nucleic acid molecule encoding a CAP and screening the mutagenized nucleic acid molecule to determine whether it encodes a mutant CAP, which can bind CD40 but lacks a CAP activity (see, for example, U.S. Pat. No. 5,223,409 and U.S. Pat. No. 5,264,563, each of which is incorporated herein by reference).

The determination that a CAP such as CAP-1 can bind CD40 or a protein having a TRAF domain provides a means to identify agents that can effectively alter the association, for example, of CAP-1 with CD40. Thus, the present invention provides a screening assay useful for identifying an effective agent, which can alter the association of CAP-1 with CD40. In addition, since CD40 is involved in apoptosis, such effective agents can be useful for modulating the level of apoptosis in a subject having a pathology characterized, for example, by an increased or decreased level of cell growth or cell proliferation.

The methods disclosed herein are useful for identifying an agent that alters the association of a CAP with a second molecule in a cell. As used herein, the term "second molecule" means a cellular molecule that can bind to a CAP. Such a second molecule can include, for example, CD40 or a TRAF domain-containing protein such as CAP-1, TRAF1 or TRAF2. A second molecule also can be a nucleotide sequence such as a DNA or RNA sequence that can bind to a CAP.

A nucleotide sequence that can bind to a CAP can be detected by using methods well known in the art (see for example, El-Deiry et al., *Nat. Gen.* 1:45 (1992), which is incorporated herein by reference). Genomic DNA can be processed to produce uniform-sized fragments using, for example, sonication, and the fragments can be screened for the ability to bind to a CAP such as CAP-1. Genomic DNA sequences that bind to a CAP can be isolated using an anti-CAP antibody followed by Protein A chromatography. Such isolated DNA sequences can be amplified by PCR, which can be facilitated by ligating the original genomic DNA fragments to "catch linkers" (El-Deiry et al., supra, 1992) suitable for annealing to PCR primers.

Alternatively, instead of screening genomic DNA fragments to identify a CAP binding nucleotide sequence, random oligonucleotides consisting of about twelve to about sixteen nucleotides, and including "catch linkers," can be screened for sequences that can bind a CAP such as CAP-1, for example, by immobilizing the CAP protein to a filter, then incubating the filter with the oligonucleotides under conditions that allow the CAP to bind relatively specifically to a CAP binding sequence. Unbound oligonucleotides can be washed from the filter, then specifically bound sequences can be eluted and amplified by PCR. Following three or more cycles of binding, elution and amplification, a consensus CAP binding sequence can be obtained. If desired, the consensus CAP binding sequence can be used to screen a genomic DNA library to obtain genomic DNA sequences containing the CAP binding sequence.

As used herein, the term "agent" means a chemical or biological molecule such as a simple or complex organic; molecule, a peptide, a peptido-mimetic, a protein, a carbohydrate or an oligonucleotide that has the potential for altering the association of a CAP with a second molecule or altering an activity of a CAP. In addition, the term "effective agent" is used herein to mean an agent that can, in fact, alter the association of a CAP with a second molecule or alter the activity of a CAP. For example, an effective agent can be one that alters the association of CAP-1 with CD40. An effective agent that alters the association of a CAP with a second molecule can interfere with the ability of a CAP to associate with the second molecule or can cause the dissociation of a bound second molecule-CAP complex, either of which can modulate the function of a cell. Thus, an effective agent can be useful as a medicament to treat pathology characterized, in part, by an abnormal cell function.

As used herein, the term "alter the association" means that the association of a CAP with a second molecule either is increased or is decreased due to the presence of an effective agent. As a result of an altered association of a CAP with a second molecule in a cell, a function of the cell can be modulated. As used herein, modulating "the function of a cell" refers to any cellular function or cell state that can be effected by a CAP in a cell including, for example, Ig class-switching, cell proliferation and apoptosis. As used herein, the term "alter the activity" means that the effective agent can increase or decrease an activity such as the signal transducing activity of a CAP in a cell. As a result of the altered activity of a CAP, the function of a cell can be modulated.

An effective agent can be useful for blocking the Ig class-switching signal that results due to the binding of CD40L of a $T_H$ cell with CD40 of a B cell. The ability to block Ig class-switching can reduce the level of IgE production by an individual, thus, providing a means to treat atopic diseases mediated by IgE class immunoglobulin. Such atopic diseases include, for example, asthma, hayfever, chronic sinusitis, skin rashes such as urticaria, or allergies such as those resulting from contact with a food, plant, plant pollen or animal dander. Similarly, autoimmune diseases, such as rheumatoid arthritis (RA), systemic lupus erythematosus (SLE), autoimmune hemolytic anemia or glomerulonephritis in which production of IgA and IgG class immunoglobulins is involved, can be treated using an effective agent that modulates Ig class-switching.

An effective agent also can be useful to decrease the proliferation of, for example, a cancer cell, which is characterized by having an increased rate of cell division or a decreased rate of cell death as compared to its normal cell counterpart. Thus, an effective agent can be used as a medicament to treat cancer by increasing the level of apoptosis in a cancer cell that expresses CD40 or a protein having a TRAF domain. An effective agent also can be useful for increasing the level of apoptosis in a cell such as a B cell in a subject having an autoimmune disease such a RA or SLE, which is characterized by an increased level of production of specific immunoglobulins that react with host tissues. Such diseases are characterized, in part, by a reduced level of apoptosis, which is a pathway ordinarily used to effectively eliminate autoreactive antibody producing B cells from an individual.

An effective agent also can be useful for decreasing the level of apoptosis or increasing Ig class-switching in B cells from a patient having an immunodeficiency, including a hereditary disorder such as X-linked hyper-IgM syndrome or an acquired disorder such as AIDS. Thus, an effective agent can be useful as a medicament for modulating apoptosis in a subject having a pathology characterized by decreased antibody production, decreased cell proliferation or increased apoptosis. In addition, an effective agent can be used to decrease the level of apoptosis and, therefore, increase the survival time of a cell such as a hybridoma cell in culture. The use of an effective agent to prolong the survival of a cell in vitro can significantly improve bioproduction yields in industrial tissue culture applications.

A mutant CAP that lacks an activity such as signal transducing activity but retains the ability to associate with a second molecule is an example of an effective agent, since the expression of a mutant CAP in a cell can alter the association of a CAP with a second molecule. Thus, it should be recognized that a mutant CAP can be an effective agent. In addition, an active fragment of a CAP can be an effective agent that alters the normal association of a CAP and a second molecule in a cell. Such active fragments, which can be peptides as small as about five amino acids, can be identified, for example, by screening a peptide library to identify peptides that can bind CD40 or a TRAF domain-containing protein (see, for example, U.S. Pat. No. 5,223, 409).

Similarly, a peptide or polypeptide portion of a second molecule can be an effective agent. For example, the C-terminal amino acid sequence of CD40 is a second molecule that can associate with CAP-1 (see Example II). A peptide derived from the C-terminal portion of CD40 can be useful, for example, for decreasing the association of wild type CD40 with CAP-1 in a cell by competing for binding to wild type CAP-1. In a similar way, a peptidomimetic can be useful as an effective agent. Such a peptido-mimetic can include, for example, a peptoid, which is a peptide-like sequence containing N-substituted glycines, or an oligocarbamate. A peptido-mimetic can be particularly useful as an effective agent due, for example, to having an increased stability to enzymatic degradation in vivo.

As disclosed herein, a screening assay can be performed in vivo using the yeast two hybrid system or can be performed in vitro. The yeast two hybrid system, for example, can be used to screen a panel of agents to identify effective agents that alter the association of a second molecule with CAP-1. As described above, a second molecule can be CAP-1 itself, a TRAF domain-containing protein, such as TRAF1, TRAF2 or CAP-1 or a nucleotide sequence that specifically binds to a CAP. An effective agent can be identified by detecting an altered level of transcription of a reporter gene. For example, the level of transcription of a reporter gene due to the bridging of a DNA-binding domain and trans-activation domain by a second molecule and CAP-1 hybrids can be determined in the absence and in the presence of an agent. An effective agent, which alters the association between a second molecule and a CAP, can be identified by a proportionately altered level of transcription of the reporter gene as compared to the control level of transcription in the absence of the agent.

In some cases, an agent may not be able to cross the yeast cell wall and, therefore, cannot enter a yeast cell to alter the association of a CAP with a second molecule. The use of yeast spheroplasts, which are yeast cells that lack a cell wall, can circumvent this problem (Smith and Corcoran, In *Current Protocols in Molecular Biology* (ed. Ausubel et al.; Greene Publ., NY 1989), which is incorporated herein by reference). In addition, an agent, upon entering a cell, may require "activation" by a cellular mechanism, which may not be present in yeast. Activation of an agent can include, for example, metabolic processing of the agent or a modification such as phosphorylation of the agent, which can be necessary to convert the agent into an effective agent. In this case, a mammalian cell line can be used to screen a panel of agents. A transcription assay such as the yeast two hybrid system described in Example I can be adapted for use in mammalian cells using well known methods (see, for example, Fearon et al., *Proc. Natl. Acad. Sci., USA* 89:7958–7962 (1992), which is incorporated herein by reference; see, also, Sambrook et al., supra, 1989; Ausubel et al., supra, 1989).

The present invention also provides in vitro screening assays. Such screening assays are particularly useful in that they can be automated, which allows for high through-put screening, for example, of randomly or rationally designed agents such as drugs, peptido-mimetics or peptides in order to identify those agents that effectively alter the association of a CAP with a second molecule and, thereby, modulate a cell function.

An in vitro screening assay can utilize, for example, CAP-1 or a CAP-1 fusion protein such as a CAP-1-glutathione-S-transferase fusion protein (GST/CAP-1; see Example II). For use in the in vitro screening assay, the CAP-1 or CAP-1 fusion protein should have an affinity for a solid substrate as well as the ability to associate with a second molecule. For example, when CAP-1 is used in the assay, the solid substrate can contain a covalently attached anti-CAP-1 antibody. Alternatively, a GST/CAP fusion protein can be used in the assay and the solid substrate can contain covalently attached glutathione, which is bound by the GST component of the GST/CAP-1 fusion protein. Similarly, a second molecule or a GST/second molecule fusion protein can be used in an in vitro assay as described herein.

An in vitro screening assay can be performed by allowing, for example, CAP-1 or a CAP-1-fusion protein to bind to the solid support as the bait protein, then adding a second molecule and an agent to be tested. Alternatively, a second molecule or a second molecule fusion protein can be used as the bait protein. Control reactions, which do not contain the agent, can be performed in parallel. Following incubation under suitable conditions, including, for example, an appropriate buffer concentration and pH and time and temperature, which allow the CAP and the second molecule to bind, the amount of CAP-1 and second molecule that have associated in the absence of an agent and in the presence of an agent can be determined and compared. The association of a CAP with a second molecule can be detected, for example, by attaching a detectable moiety such as a radionuclide or a fluorescent label to the second molecule and measuring the amount of label that is associated with the solid support, wherein the amount of label detected indicates the amount of association of the second molecule with the CAP. By comparing the amount of specific binding in the presence of an agent as compared to the control level of binding, an effective agent, which alters the association of a CAP with a second molecule, can be identified. Such an assay is particularly useful for screening a panel of agents such as a peptide library in order to detect an effective agent.

The methods for identifying an effective agent that alters the association of a CAP with a second molecule, as described above, can be used to determine whether the agent can dissociate a bound second molecule/CAP-1 complex. For this purpose, a CAP is contacted with second molecule under conditions suitable for forming a second molecule/CAP complex, then the complex is contacted with the agent. The method can be performed using an in vitro or in vivo assay as described above and an effective agent can be identified by its ability to dissociate the bound complex.

The above described in vivo and in vitro assays also can be used to identify a CAP other than CAP-1. In particular, the yeast two hybrid system can be performed using CD40 as the "bait" protein to screen a cDNA expression library derived from various types of CD40 expressing cells (see Example I). For in vitro screening, proteins encoded in the cDNA library can be expressed as fusion proteins on the surface of a non-filamentous phage particle and then screened for binding to CD40 to identify a CAP other than CAP-1 (see U.S. Pat. No. 5,223,409). Similar assays can be performed using a protein having a TRAF domain as the bait protein.

The in vivo and in vitro assays disclosed herein also can be used to identify a second molecule that binds to a CAP. For example, a second molecule such as a TRAF domain containing protein can be detected using the yeast two hybrid assay where a CAP such as CAP-1 is used as the "bait" protein. A TRAF domain-containing protein can be useful for modulating the activity of a CAP in a cell and effect the function of the CAP to mediate signal transduction from CD40. The identification of a second molecule that can bind to a CAP provides an additional target for modulating a cell function by contacting the cell, for example, with an effective agent that alters the association between the CAP and the second molecule.

The invention also provides a method for identifying an effective agent that alters the association between CAP-1 and a second molecule in a test sample containing CAP-1 and the second molecule. As used herein, the term "test sample" means a cell or tissue specimen obtained from a subject such as a subject suspected of having a pathology characterized by an altered cell function such as altered levels of Ig class-switching, cell proliferation or apoptosis. A test sample can be obtained, for example, during surgery or by needle biopsy. The test sample can be, for example, a soluble lysate, which is obtained by treating a cell sample with a solubilizing agent such as a non-ionic detergent.

A soluble lysate or other test sample can be examined using a gel shift assay to determine whether a CAP and a second molecule are present in the cell sample and associated as a bound complex. For example, the test sample can be fractionated by electrophoresis in a non-denaturing gel such as a low percentage polyacrylamide gel using a buffer containing 50 mM Tris (pH 8.5), 0.4 M glycine, 2 mM EDTA and 3% glycerol. Buffer conditions, gel concentration or other parameters of electrophoresis can be optimized using well known methods such that electrophoretic separation of the free second molecule, free CAP and second molecule/CAP complex in the test sample is achieved. The identity of the free and bound molecules can be determined by western blotting using antibodies specific for the second molecule or the CAP. Methods for performing western blotting, such as with enzyme or radioisotope labelled primary or secondary antibodies are well known in the art (see, for example, Harlow and lane, supra 1988). The gel shift assay can be useful for identifying an agent that alters the association of a CAP with a second molecule by contacting a portion of a test sample with an agent and comparing the bound and free molecules in the treated sample with an untreated control sample.

The invention further provides methods for identifying an agonist that can increase the level of expression of a CAP in a cell. An agonist can be introduced into a cell and, by increasing the level of expression of a CAP in the cell, can modulate a function of a cell. As used herein, "CAP agonist" means a chemical or biological molecule such as a simple or complex organic molecule, a peptide, peptido-mimetic, protein, carbohydrate or nucleotide sequence that can increase the expression or activity of CAP, which can effect the level of apoptosis in a cell.

A nucleic acid molecule that encodes CAP-1 and that can be introduced into and expressed in a cell is an example of a CAP agonist. A CAP agonist also can include a hormone, cytokine or other type of molecule that interacts directly or indirectly, for example, with genetic regulatory elements that control expression of a CAP in a cell. Such genetic regulatory elements include, for example, promoters, enhancers, silencers or intron sequences, which can regulate protein expression at the transcriptional or translational level. For example, a CAP-1 agonist can increase the expression of CAP-1 in a cell by binding to the promoter region of the CAP-1 gene and increasing the level of transcription. A CAP-1 agonist also can increase the expression of CAP-1 indirectly by binding to a regulatory protein, which, in turn, can increase transcription of the CAP-1 gene.

The invention further provides methods for modulating the level of apoptosis in a cell by contacting the cell with a CAP antagonist. As used herein, "CAP antagonist" means a chemical or biological molecule such as a simple or complex organic molecule, a peptide, peptidomimetic, protein, carbohydrate or nucleotide sequence that can decrease the expression or activity of a CAP, which can modulate a function of a cell.

A CAP antagonist can be, for example, an antisense nucleotide sequence or a ribozyme, which is complementary to and can hybridize to a portion of a nucleic acid sequence encoding a CAP. Such a nucleic acid sequence can be, for example, the CAP-1 gene or a CAP-1 mRNA transcribed from the gene. Such a CAP antagonist can be introduced into the cell and, if desired, can be expressed in the cell. The CAP antagonist can decrease the expression of the CAP in a cell, which can alter the normal steady-state association of the CAP with a second molecule, thereby modulating a function of the cell.

A CAP antagonist also can include a hormone, cytokine or other molecule that interacts directly or indirectly, for example, with genetic regulatory elements in a cell that result in a decreased level of expression of the CAP. Such genetic regulatory elements include, for example, a genetic promoter, enhancer, silencer or intron sequence, which can regulate protein expression at the transcriptional or translational level. For example, a CAP antagonist can decrease the expression of CAP-1 in a cell by binding to the promoter region of the CAP-1 gene, thereby, decreasing the efficiency of transcription. A CAP antagonist also can decrease the expression of a CAP indirectly by binding to a regulatory protein required to activate an enhancer sequence involved in transcription of the CAP gene. A CAP agonist or CAP antagonist as disclosed herein can be useful as a medicament for treating a pathology characterized by an increased or decreased cell function as compared to its normal cell counterpart.

A nucleic acid sequence encoding a CAP can be expressed in a cell using well known expression vectors and gene transfer methods (see Sambrook et al., supra, 1989). Viral vectors that are compatible with a targeted cell are particularly useful for introducing a nucleic acid encoding a CAP into a cell. For example, recombinant adenoviruses having general or tissue-specific promoters can be used to deliver a nucleic acid encoding CAP-1 into a variety of cell types in various tissues and can direct expression of the nucleic acid in the target cell. Recombinant adeno-associated viruses also are useful for introducing a nucleic acid encoding a CAP into a cell and have the added advantage that the recombinant virus can stably integrate into the chromatin of even quiescent non-proliferating cells such as neurons of the central and peripheral nervous systems (Lebkowski et al., *Mol. Cell. Biol.* 8:3988–3996 (1988), which is incorporated herein by reference).

Such viral vectors are particularly useful where it is desirable to introduce a nucleic acid encoding a CAP into a cell in a subject, for example, for gene therapy. Viruses are specialized infectious agents that can elude host defense mechanisms and can infect and propagate in specific cell types. In particular, the specificity of viral vectors for particular cell types can be utilized to target predetermined cell types. Thus, the selection of a viral vector will depend, in part, on the cell type to be targeted. For example, if a neurodegenerative disease is to be treated by increasing the level of a CAP in neuronal cells affected by the disease, then a viral vector that targets neuronal cells can be used. A vector derived from a herpes simplex virus is an example of a viral vector that targets neuronal cells (Battleman et al., *J. Neurosci.* 13:941–951 (1993), which is incorporated herein by reference). Similarly, if a disease or pathological condition of the hematopoietic system is to be treated, then a viral vector that is specific for a particular blood cell or its precursor cell can be used. A vector based on a human immunodeficiency virus is an example of such a viral vector (Carroll et al., *J. Cell. Biochem.* 17E: 241 (1993), which is incorporated herein by reference). In addition, a viral vector or other vector can be constructed to express a nucleic acid encoding a CAP in a tissue specific manner by incorporating a tissue-specific promoter or enhancer into the vector (Dai et al., *Proc. Natl. Acad. Sci., USA* 89:10892–10895 (1992), which is incorporated herein by reference).

Retroviral vectors can be particularly useful for introducing a nucleic acid encoding a CAP into a cell in vivo. Retroviral vectors can be constructed either to function as infectious particles or to undergo only a single initial round of infection. In the former case, the genome of the virus is modified so that it maintains the necessary genes, regulatory sequences and packaging signals to synthesize new viral proteins and RNA. However, genes conferring oncogenic potential of these viruses is destroyed. After the viral proteins are synthesized, the host cell packages the RNA into new viral particles, which can undergo further rounds of infection. The viral genome also is engineered to encode and express the desired recombinant gene.

In the case of non-infectious viral vectors, the helper virus genome can be mutated to destroy the viral packaging signal required to encapsulate the RNA into viral particles. However, the helper virus retains structural genes required to package a co-introduced recombinant virus containing a gene of interest. Without a packaging signal, a viral particle will not contain a genome and, thus, cannot proceed through subsequent rounds of infection. Methods for constructing and using viral vectors are known in the art and reviewed, for example, in Miller and Rosman, *Biotechniques* 7:980–990 (1992), which is incorporated herein by reference. The specific type of vector will depend upon the intended application. These vectors are well known and readily available within the art or can be constructed by one skilled in the art.

For gene therapy, a vector containing a nucleic acid encoding a CAP or CD40 or an antisense nucleotide sequence or ribozyme can be administered to a subject by various methods. For example, if viral vectors are used, administration can take advantage of the target specificity of the vectors. In such cases, there is no need to administer the vector locally at the diseased site. However, local administration can be a particularly effective method of administering a nucleic acid encoding a CAP or an appropriate antisense or ribozyme sequence as described above. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule encoding a CAP into cells in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference). Direct injection of a naked nucleic acid molecule or a nucleic acid molecule encapsulated, for example, in cationic liposomes also can be used for stable gene transfer into non-dividing or dividing cells in vivo (Ulmer et al., *Science* 259:1745–1748 (1993), which is incorporated herein by reference). In addition, a nucleic acid molecule encoding a CAP can be transferred into a variety of tissues using the particle bombardment method (Williams et al., *Proc. Natl. Acad. Sci.. USA* 88:2726–2730 (1991), which is incorporated herein by reference). Such nucleic acid molecules can be linked to the appropriate nucleotide sequences required for transcription and translation.

A particularly useful mode of administration of a nucleic acid encoding a CAP is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promotor, an enhancer or other expression element specific for the desired subset of cells can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

An alternative method of modulating apoptosis, proliferation or differentiation in a cell is to introduce a nucleotide sequence encoding an antisense CAP, CD40 or other second molecule or a ribozyme specific for an mRNA encoding a CAP, CD40 or other second molecule into the cell. Such a nucleotide sequence can be introduced into a cell using the methods and vectors described above. Chemically synthesized nucleotide sequences also can be administered directly to cells. Synthetic antisense or ribozyme oligonucleotides can be prepared using well known methods or can be purchased from commercial sources and, if desired, can incorporate nucleotide analogs to increase the resistance of the oligonucleotide to degradation by nucleases in a cell. Synthetic antisense or ribozyme sequences can be active in a cell after contact with and uptake by the cell.

A nucleic acid CAP agonist or antagonist can be introduced into a cell using the procedures described above. In addition, these or other CAP agonists or antagonists of the present invention can be contacted directly with a cell in vitro or can be administered in vivo as a pharmaceutical composition containing the antagonist or agonist and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of a CAP-1 antagonist or agonist. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. One skilled in the art would know that a pharmaceutical composition containing a CAP antagonist or agonist can be administered to a subject by various routes including, for example, by direct instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to modulate apoptosis, a CAP agonist or CAP antagonist is administered in an effective amount, which can be determined by methods known to those in the art. As used herein, the term "effective amount" means the amount of agonist or antagonist that can have a functional effect on a cell by modulating the level of apoptosis of the cell. An effective amount of a CAP agonist or antagonist administered in vivo is an amount that reduces symptoms associated with the disease being treated.

The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of CAP-1 agonist or antagonist required to obtain an effective dose in a subject depends on many factors including the age and general health of the subject as well as the route of administration and the number of treatments to be administered, as well as the chemical form of the antagonist or agonist. In view of these factors, the skilled artisan would adjust the particular amount so as to obtain an effective amount for subject being treated.

The present invention also provides methods for detecting the presence of a CAP such as CAP-1 in a test sample by detecting the CAP protein or a nucleic acid molecule encoding the CAP. In addition, the invention provides methods for diagnosing a pathology that is characterized, in part, by an increased or decreased cell function to determine whether the abnormal cell function is due, for example, to increased or decreased expression of CAP-1 in the cell or to expression of a mutant CAP-1. The identification of such a pathology can allow for intervention therapy using an effective agent or a nucleic acid molecule or an antisense nucleotide sequence as described above.

In order to diagnose a pathology that is characterized, in part, by an altered cell function, which can be due to altered expression of a CAP, a test sample can be obtained from a subject having the pathology and can be compared to a control sample, which is obtained from a normal subject. The level of a CAP in the test sample can be compared to the level in the normal sample.

The level of a CAP in a cell can be determined by contacting a sample with a reagent such as an anti-CAP antibody, CD40 or other second molecule, which can specifically bind a CAP. For example, the level of CAP-1 in a cell can determined by well known immunoassay or immunohistochemical methods using an anti-CAP-1 antibody (see, for example, Reed et al., supra, 1992; see, also, Harlow and Lane, supra, 1988). As used herein, the term "reagent" means a chemical or biological molecule that can specifically bind to a CAP or to CD40 or to a bound CAP/CD40 complex. For example, an anti-CAP-1 antibody or CD40 can be a reagent for CAP-1 and an anti-CD40 antibody or CAP-1 can be a reagent for CD40.

Increased or decreased expression of a CAP in a cell in a test sample can be determined by comparison to an expected normal level for the CAP in a particular cell type. A normal range of particular CAP levels in various cell types can be determined by sampling a statistically significant number of normal subjects. In addition, a control sample can be evaluated in parallel with a test sample in order to determine whether a pathology characterized by increased or decreased apoptosis is due to increased or decreased expression of a CAP. The test sample can be examined using, for example, immunohistochemical methods as described above or the sample can be further processed and examined. For example, an extract of a test sample can be prepared and examined to determine whether a CAP that is expressed in a cell in the sample can associate with CD40 in the same manner as a CAP from a control cell or whether, instead, a variant CAP is expressed in the cell.

A diagnostic assay kit incorporating a reagent such as an anti-CAP antibody, CD40 or other second molecule, which can specifically bind a CAP, can be useful for detecting a pathology due to altered CAP expression in a cell. Such a kit is particularly useful because it allows for standardization of assay conditions. A kit can contain, in addition to a reagent, a reaction cocktail that provides suitable reaction conditions for performing the assay and control sample that contains a known amount of a CAP. If desired, the kit can contain an antibody that is specific and can specifically bind the reagent.

A diagnostic assay should include a simple method for detecting the amount of a CAP in a sample that is bound to the reagent. Detection can be performed by labelling the reagent and detecting the presence of the label using well known methods (see, for example, Harlow and Lane, supra, 1988; chap. 9). A reagent can be labelled with various detectable moieties including a radiolabel, an enzyme, biotin or a fluorochrome. Materials for labelling the reagent can be included in the diagnostic kit or can be purchased separately from a commercial source. Following contact of a labelled reagent with a test sample and, if desired, a control sample, specifically bound reagent can be identified by detecting the particular moiety.

A labelled antibody that can specifically bind the reagent also can be used to identify specific binding of an unlabelled reagent. For example, if the reagent is an anti-CAP-1 antibody, a second antibody can be used to detect specific binding of the anti-CAP-1 antibody. A second antibody generally will be specific for the particular class of the first antibody. For example, if an anti-CAP-1 antibody is of the IgG class, a second antibody will be an anti-IgG antibody. Such second antibodies are readily available from commercial sources. The second antibody can be labelled using a detectable moiety as described above. When a sample is labelled using a second antibody, the sample is first contacted with a first antibody, then the sample is contacted with the labelled second antibody, which specifically binds to the first antibody and results in a labelled sample.

A method for determining the level of expression of a nucleic acid molecule encoding a CAP also is useful for diagnosing a pathology characterized by an abnormal level of expression of a CAP. For example, a target nucleic acid molecule such as a DNA or RNA sequence encoding a CAP can be detected in a sample using a complementary nucleotide sequence. The target nucleic acid molecule can be extracted from a sample by methods well known in the art (see Sambrook et al., supra, 1988). Methods to detect the presence of a particular nucleic acid molecule within a population of nucleic acid molecules are well known to those in the art and include, for example, Southern blotting, northern blotting, slot blotting and PCR amplification (see, for example, Sambrook et al., supra, 1989). In situ hybridization also can be used to identify nucleic acids in a sample (see, for example, Pardue, in *Nucleic Acid Hybridization: A practical approach* (IRL Press, 1991), which is incorporated herein by reference).

To detect a nucleic acid molecule encoding a CAP in a sample, the sample is contacted with the complementary nucleotide sequence that can hybridize to a nucleic acid molecule encoding the CAP under relatively stringent conditions. The nucleotide sequence can carry a detectable label, such as a radioisotope. The presence of a nucleic acid molecule encoding the CAP in the sample can be determined, for example, by detecting the level of the specifically bound nucleotide sequence. The normal level of binding of the nucleotide sequence also can be determined in a control sample, which is obtained from a normal subject and contains a normal level of the CAP encoding nucleic acid molecules. An increase or a decrease in the level of nucleic acid molecules encoding a CAP in the test sample compared to the normal level present in the control sample indicates a pathology characterized by an abnormal expression of the CAP. A complementary nucleotide sequence for a CAP can also be used as a primer in a PCR reaction to detect the level of nucleic acid molecules in a sample encoding the CAP.

The following examples are intended to illustrate but not limit the invention.

EXAMPLE I

Identification of Cap-1 Using the Yeast Two Hybrid System

This example demonstrates the use of the yeast two hybrid system to identify cDNA sequences encoding proteins that can associate with the cytoplasmic domain of CD40.

A. Host/Vector System

The "L40 system" was used to identify cDNA sequences encoding CD40 associated proteins. *S. cerevisiae* strain L40 yeast cells were used as the host cells for the two hybrid assay ("L40 system;" Vojtek et al., supra, (1993)). Strain L40 cells have a MATa, trp1, leu2, his3, ade2, LYS2: (lexAop) 4-HIS3, URA3::(lexAop) 8-lacZ genotype and are stably transformed with histidine synthetase (HIS3) and lacZ reporter genes, both of which are under the control of a lexA operator. Strain L40 cells were grown in YPD medium.

Figure 4:
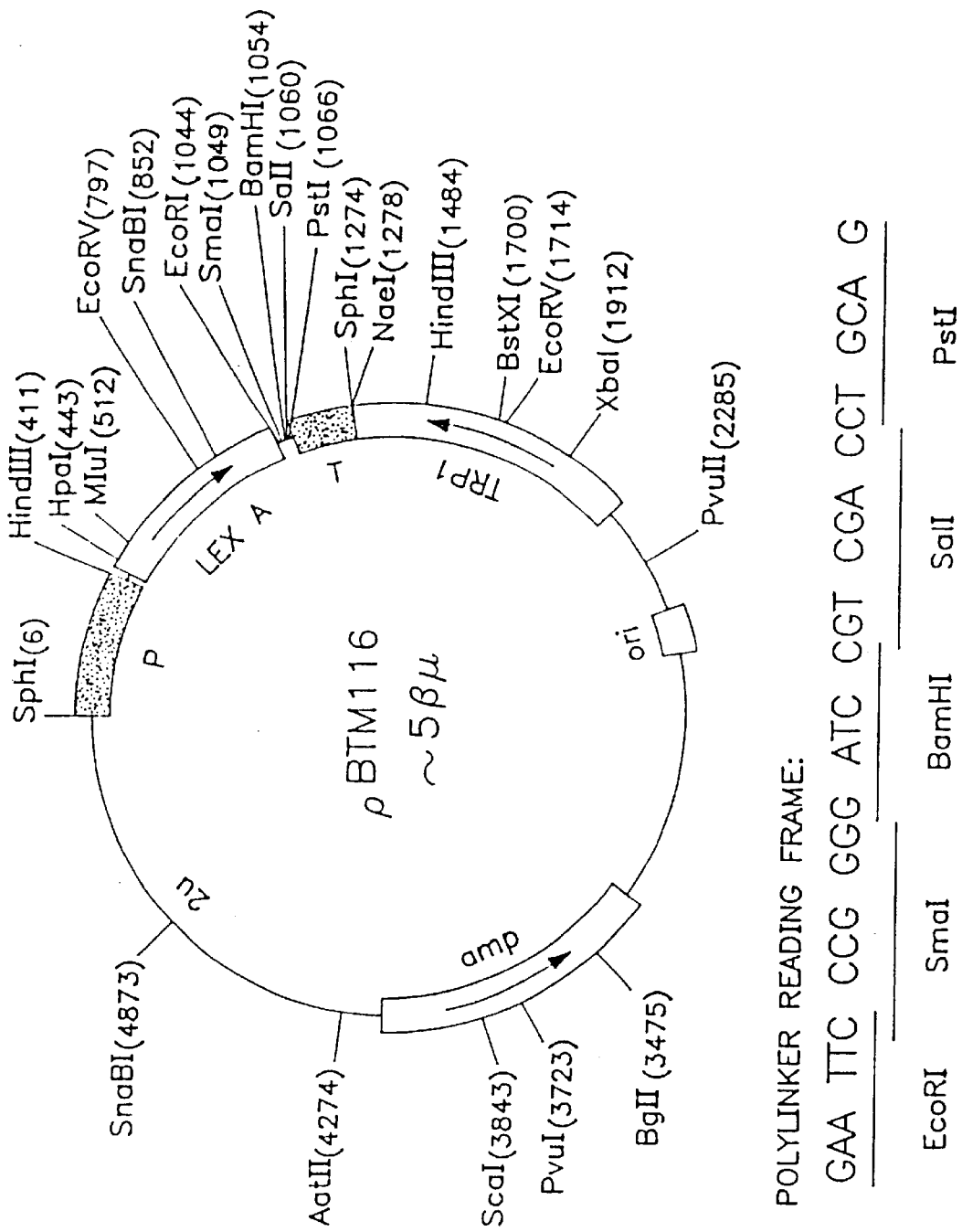
FIG. 4 provides a map of plasmid pBTM-116, which was used to produce LexA/CD40 fusion proteins. The plasmid contains a bacterial origin of replication (ori) and an ampicillin resistance gene (amp). The plasmid also contains a yeast 2 micron (2 μm) origin of replication and a gene that allows a yeast cell containing the plasmid to grow in the absence of tryptophan (TRP1). A LexA/CD40 fusion protein was produced by inserting a nucleotide sequence (SEQ ID No: 17 encoding the cytoplasmic domain of CD40 into the EcoRI/BamHI sites located in the multiple cloning site.

The "bait" protein in the yeast two hybrid system was expressed from the plasmid pBTM-116 (Vojtek et. al., supra, 1993). The bait protein, when expressed, contains a LexA DNA binding motif and, thus, associates directly with DNA acting as bait for another binding protein. The Plasmid pBTM-116 encodes the LexA DNA-binding domain under control of an ADH promotor (FIG. 4). The presence of pBTM-116 in strain L40 cells permits the cells to grow in tryptophan-deficient medium.

Plasmid pACT, also known as pSE1107, contains a promoter-controlled GAL4 trans-activating domain (see Durfee et al., supra, 1993). The presence of pACT in strain L40 cells permits the cells to grow in leucine-deficient medium. Physical association of the GAL4 trans-activating domain with the DNA binding domain of LexA results in a functional transcriptional activator.

B. Preparation of Vectors Encoding Hybrid Proteins

A cDNA library derived from a human B cell was constructed in the λ-derived expression vector pACT as described previously (Durfee et al., supra, 1993). The various cDNA sequences were cloned in-frame to an upstream GAL4 trans-activating gene sequence.

The cDNA encoding two cytosolic fragments of CD40 (positions 216–277 and positions 225–269) were generated by PCR from the plasmid pCDM8-CD40 (Stamenkovic et al., *EMBO J.* 8:1403–1410 (1989), which is incorporated herein by reference) using the following primers containing Eco RI (underlined) and Bcl I (italic) sites (bold indicates stop codon): CD40 (positions 216–277), 5'-G GAATTCAAAAAGGTGGCCAAG-3' (forward primer; SEQ ID NO: 3) and 5'-TGATCATCACTGTCTCTCCTGCAC-3' (reverse primer; SEQ ID NO: 4); and CD40 (positions 225–269), 5'-GGAATTCAAGGCCCCCCACCCCAAG-3' (forward primer; SEQ ID NO: 5) and 5'-TGATCAACTCTCTTTGCCATCCTC-3' (reverse primer; SEQ ID NO: 6). The PCR products were digested with Eco RI and Bcl I, then directly cloned into the Eco RI and Bam HI sites of the yeast two hybrid plasmid pBTM-116 in-frame with the upstream LexA DNA-binding domain sequences (Vojtek et al., supra, 1993).

For expression of LexA-Fas, a cDNA sequence encoding a cytoplasmic domain fragment of Fas (positions 191–335; Itoh et al., supra, 1991) was generated by PCR (Higuchi et al., supra, 1990) from plasmid pBSAP014.1 (Oehn et al., *J. Biol. Chem.* 267: 10709–10715 (1992) and Sato et al., *Proc. Natl. Acad. Sci. (USA)* 91:9238–9242 (1994), both of which is incorporated herein by reference) using the following primers containing Eco RI (underlined) and Bcl I (italics) sites (bold indicates STOP codon, TCA), as follows: 1) 5'-G GAATTCAAGAGAAAGGAAGTACAG-3' (forward primer; SEQ ID NO: 7); 2) 5'-GTGATCACTAGACCAAGCTTTGGAT (reverse primer; SEQ ID NO: 8). The PCR product was digested with Eco RI and Bcl I and cloned into EcoRI/BamHI digested pBTM-116 to produce pBTM/CD40 (positions 191–335).

For expression of a LexA-TNF-R2 fusion protein, the cytosolic domain of TNF-R2 (positions 228–461) was amplified by PCR from a p-Bluescript-p80-TNF-R2 plasmid (Smith et al., *Science* 248:1019–1023 (1990), which is incorporated herein by reference) using the following primers containing Eco RI (underlined) and Sal I (italics) sites (bold indicates a stop codon, TTA) 5'-G GAATTCAAAAAGAAGCCCTTGTGCCT-3' (forward primer; SEQ ID NO: 9) and 5'-GGTCGACTTAACTGGGCTTCATCCCA-3' (reverse primer; SEQ ID NO: 10). The PCR product was digested with Eco RI and Sal I and cloned into EcoRI/XhoI-digested pBTM-116 to produce pBTM/TNF-R2 (positions 228–461).

Additional pBTM-116 plasmids encoding portions of the Bcl-2 (positions 83–218), Ha-Ras (V12), and Lamin-C proteins were produced as described previously (Sato et al., supra, 1994; Vojtek et al. supra, 1993).

C. Assay Methods

Plasmid DNA was transformed into yeast cells by the LiCl method (Gietz et al., *Nucl. Acids Res.* 20:1425 (1992); Schiestl et al., *Curr. Genet.* 16:339–346 (1989), each of which is incorporated herein by reference). 0.5 mg of pACT-cDNA library DNA mixed with 1 mg of denatured salmon sperm carrier DNA was used for transformation of ~5×10$^9$ L40-strain cells. Transformed cells were grown in complete minimal medium lacking tryptophan or leucine as necessary to select for the presence of pBTM or pACT derived plasmids, respectively. In addition, growth in histidine-deficient medium indicated formation of transcriptionally active LexA/GAL4 complex.

D. Selection of CAP Candidates

The pBTM/CD40 (positions 216–277) plasmid was introduced into L40 cells, which contain histidine synthetase (HIS3) and β-galactosidase (lacZ; β-gal) reporter genes under the control of lexA operators. The resulting transformants were selected for ability to grow on medium lacking tryptophan, since the pBTM-116 plasmid contains a TRP1 gene that complements the defect in the host strain. L40 cells containing the pBTM/CD40 (positions 216–277) then were transformed with the pACT-B cell cDNA library. Transformants containing both pBTM and pACT plasmids were selected by growth on media lacking both leucine and tryptophan.

Colonies expressing a cDNA sequence encoding a candidate CAP were identified initially by their ability to grow in medium lacking histidine due to expression of the lexAop/HIS3 reporter gene construct in the yeast cells. Approximately 31 million transformants were screened and 2,640 His+ colonies were identified. These 2,640 clones were examined further using a β-gal colorimetric filter assay as described previously (Sato et al., supra, 1994) to identify expression of the lacZ reporter gene, which is under the control of a lexA operator. Following this second screening procedure, 166 positive clones were obtained.

The 166 clones were cured of LexA/CD40-encoding plasmids by growing the cells in tryptophan-containing medium. The cured cells then were mated against a panel of a-type yeast (strain NA-8711-A (a, leu2, his3, trp1, pho3, pho5)) plasmids containing one of the following LexA fusion proteins: cytosolic domain of CD40 (positions 216–277), CD40 (positions 225–269), cytoplasmic domain of Fas (positions 191–335), Bcl-2 (positions 83–218) Ras V12 and Lamin C. The mated cells were selected for growth in medium lacking tryptophan and leucine to obtain cells that contained both a pACT-B cell clone and a LexA-fusion protein. Colonies were transferred to histidine-deficient plates or histidine-containing media with X-Gal. Colonies expressing β-gal activity were identified using a plate assay and a filter assay. The plate assay was performed on the X-Gal containing plates ~12 hr after plating according to previous methods (see Chien et al., Proc. Natl. Acad. Sci., USA 88:9578–9582 (1991), which is incorporated herein by reference). The β-gal filter assay was performed after 1 hr culture as described previously (Sato et al., supra, 1994; Breeden and Nasmyth, Cold Spring Harbor Symp. Quant. biol. 50:643–650 (1985), which is incorporated herein by reference).

Of the 166 clones tested, two clones were found (pACT121 and pACT2229) that reacted with the LexA/CD40 protein but not with the other fusion proteins (see Table 1). DNA sequence analysis showed that the two clones contained identical cDNA inserts fused to the upstream GAL4 trans-activating domain, suggesting that the two clones arose as library-amplified copies of a single cDNA. The sequence of the cDNA inserts of the two clones showed an open reading frame of 543 base pairs (bp; 181 amino acids) followed by a stop codon and 3' untranslated region of ~457 bp. The cDNA was named CAP-1 for CD40 associated protein-1.

TABLE I

INTERACTION OF CAP-1 (pACT2229/GAL4 FUSION) WITH VARIOUS LexA FUSION PROTEINS

| pBMT-116 (LexA FUSION) | HIS⁻ Growth | β-GAL |
|---|---|---|
| CD40 (216–277) | + | + |
| CD40 (225–269) | + | + |
| TNFR2 (288–461) | – | – |
| Fas (191–335) | – | – |
| Ras (V12) | – | – |
| Bcl-2 (83–218) | – | – |
| Lamin-C | – | – |

EXAMPLE II

In Vitro Assays to Identify a CAP

This example describes methods for constructing fusion proteins and producing labelled proteins useful for detecting and characterizing a CAP in vitro.

A. Production of GST Fusion Proteins

GST-fusion proteins were cloned into pGEX plasmids (Pharmacia, Piscataway, N.J.) and expressed in E. coli. pBTM 116-CD40 (positions 225–269), Fas and TNF-R2 plasmids were digested with Eco RI and either Xho I or Sal I and the inserts subcloned in-frame with the upstream GST sequences in pGEX-4T-1. For GST-CD40 (positions 220–277), a Bal I fragment encoding amino acids 220–277 was excised from pCDM8-CD40 and subcloned initially into the Hinc II site of Bluescript pSKII (Stratagene, Inc.; La Jolla Calif.). The pSKII-CD40/BalI plasmid was then cut with XhoI and EcoRI and the fragments containing CD40 sequences were each subcloned into a modified version of pGEX-2T-1 in-frame with the GST sequence. For GST-TNF-R1, the cytoplasmic domain of TNF-R1 was PCR amplified from the plasmid pUC19-p55-TNF-R1 (Loetscher et al., Cell 61:351–359 (1990), which is incorporated herein by reference) using the following primers 5'-GGGATCCGCTACCAACGGTGGAAG-3' (forward primer; SEQ ID NO: 11) and 5'-GGTCGACTCATCTGAGAAGACTGGG-3' (reverse primer; SEQ ID NO: 12), digested with Bam HI and Sal I and subcloned into pGEX-5X -1. For GST-CAP-1, the pACT2229 cDNA was digested with Bgl II, and the CAP-1 cDNA (positions 363–543) was subcloned into pGEX-3X.

GST-fusion proteins were produced in either DH5-α-F' or HB101 cells transformed with pGEX plasmids. Overnight cultures were diluted 1:10 into LB medium containing 50 µg/ml ampicillin to make 0.5 liter cultures and were incubated at 30° C. and 250 revolutions per minute (rpm) for an additional 2 hr, after which isopropyl β-D-thiogalactopyranoside (IPTG) was added (1 mM) and the cultures were incubated for 8 to 16 hr further at 30° C. and 250 rpm. Cells were recovered by centrifugation, resuspended in ~10 ml of phosphate buffered saline (PBS) pH 7.4 (12.5 mM $NaPO_4$ and 0.15 M NaCl) containing 1% Triton-X100, 1 mM PMSF, and 1 mg/ml lysozyme and sonicated on ice using 5 bursts of 30 seconds each from a 1.6 mm tip (Ultrasonicator Model XL-2020; Heat Systems, Inc., Farmingdale N.Y.). After centrifugation at 8,000×g for 10 min, the resulting supernatant was mixed with 1 ml of glutathione-Sepharose 4B (Pharmacia, Inc.) for 1 hr at 4° C. The beads were washed 2× in PBS containing 1% Triton-X100 and the amount of bound GST protein was estimated by sodium dodecyl sulfate polyacrylamide gel electrophoresis (SDS-PAGE) and Coomassie-blue staining of a sample of the protein released by boiling an aliquot of the beads in SDS sample buffer (see Harlow and lane, supra, 1988).

B. Characterization of CAP Binding to CD40

The disclosed methods demonstrate in vitro binding between CAP-1 and CD40.

1. Labelling of CAP-1

The CAP-1 cDNA was PCR amplified using a forward primer containing a T7 promoter (5'-TAATACGACTCACTATAGGGAGACCA-CATGGATGATGTATATAACTATC ATTTC-3'; SEQ ID NO: 13) and a reverse primer (5'-CTACCAGAATTCGGCATGCCGGTAGAGGTGTGGTCA-3'; SEQ ID NO: 14) from 1 µg pACT2229 plasmid DNA. One-tenth of the resulting PCR product (approximately 0.1 µg) was then directly transcribed and translated in vitro in the presence of $^{35}$S-methionine using 12.5 µl of reticulocyte lysate (TNT-Lysate®; Promega, Inc.; Madison, Wis.).

2. Binding of Labelled CAP-1 to GST Fusion Proteins

Glutathione-Sepharose beads containing 5 µg of GST fusion proteins (i.e., bait proteins) were incubated with 10 µl in vitro-translated $^{35}$S-CAP-1 protein for 16 hr at 4° C. in a buffer containing 50 mM Tris pH 8.0, 150 mM NaCl, 5 mM DTT, 2 mM EDTA, 0.1% NP-40, 1 mM PMSF and 1 µg/ml leupeptin. The beads were washed vigorously 5× in the above buffer, pelleted by centrifugation, boiled in SDS-PAGE sample buffer and analyzed by SDS-PAGE and fluorography (Harlow and Lane, supra, 1988). The binding results (not shown) indicated that CAP-1 interacted specifically with GST-fusion proteins containing the nearly full-length CD40 cytoplasmic domain (positions 220–277) as well as the conserved subregion of the CD40 cytosolic domain (positions 225–269). No interactions were detected between CAP-1 and GST-fusion protein containing the cytosolic domains of Fas, TNF-R1, or TNF-R2 as well as GST itself. Interestingly, CAP-1 did interact with GST-CAP-1, implying that CAP-1 can homodimerize. The specificity of these results was further confirmed by experiments where a variety of other $^{35}$S-labeled in vitro-translated proteins, including Bcl-2, Bax, Lyn were found not to bind to the above GST-CD40 fusion proteins under the same conditions used for binding to $^{35}$S-CAP-1 (data not shown).

3. Binding of GST-CAP-1 to CD40 from a Cell Lysate

For experiments with cell lysates, 2×10$^7$ RS11846 B-cell lymphoma cells were lysed in 0.25 ml of ice-cold Tris buffered saline (TBS) pH 7.4 (10 mM Tris and 150 mM NaCl) including 5 mM EDTA, 1% Triton-X100, with protease inhibitors PMSF, aprotinin, leupeptin, benzamidine, and pepstatin. Nuclei and cellular debris were removed from the cell lysate by centrifugation as described (Reed et al., *Canc. Res.* 51:6529–6538 (1991)). The resulting supernatants were then incubated with either 5 μg of affinity-purified GST-CAP-1 (positions 363–543) or GST as a control protein (bait proteins) immobilized on 50 μl of glutathione-Sepharose beads for ~16 hr at 4° C., then washed 10× in 50 mM Tris pH 7.4 containing 150 mM NaCl, 5 mM EDTA, 0.1% NP-40, 1 mM PMSF, 1 μg/ml leupeptin. Proteins adsorbed to beads were eluted by boiling in SDS-PAGE sample buffer, electrophoresed in SDS-PAGE gels containing 12% acrylamide and then transferred to nitrocellulose for western blotting. The resulting blots were preblocked in TBS buffer containing 5% non-fat milk and 3% bovine serum albumin and then incubated with 2 μl/ml of anti-human CD40 monoclonal antibody B-B20 (Biosource, Inc., Camarillo Calif.) followed by horseradish peroxidase-conjugated goat anti-mouse IgG (see Reed et al., supra, 1992; Hanada et al., *Canc. Res.* 53:4978–4986 (1993), which is incorporated herein by reference). The presence of bound peroxidase was detected using an emission chemiluminescence method performed according to the manufacturer's instructions (Amersham, Inc., Arlington Heights Ill.)

Western blotting with the anti-CD40 antibody identified a band in the lymphoma cell lysate of about 50 kda indicating the presence of CD40 in the lysate. A similar size band was seen in the lane where the lysate was reacted with the GST-CAP-1 fusion protein but not in the lane where the GST-control protein was reacted with the lysate, indicating that the GST-CAP-1 can bind specifically to CD40 in the cell lysate.

C. Screening a cDNA Expression Library

A cDNA library can be screened to identify a new CAP or to identify clones providing further cDNA sequence to complete the open reading frame (ORF) of the partial cDNA clone that was used to screen the library.

To identify a new CAP, a $^{32}$P-labeled GST/CD40 protein can be used for direct screening of a λgt11 cDNA expression library, which can be obtained from a commercial source (Clontech; Palo Alto Calif.) or constructed using well known methods (Sambrook et al., supra, 1989). Radiolabeled GST control protein or GST/CD40 is obtained as described above. Phage containing the library clone sequences are transferred to nitrocellulose filters, which are placed in a plastic bag. Hybridization buffer (1% milk, 20 mM Hepes-KOH, pH 7.7, 75 mM KCl, 0.1 mM EDTA, 2.5 mM MgCl$_2$) is added and approximately 250,000 cpm/ml GST/CD40 (or GST) are added. Filters are incubated at 4° C., overnight, in the presence of a 20-fold molar excess of unlabeled GST protein (see, for example, Kaelin et al., supra, 1992).

Positive plaques are selected and subjected to further rounds of screening as above. After 3–4 rounds of screening, the cDNA inserts of plaque purified phages are amplified by PCR using primers that flank the vector cloning site or, alternatively, are liberated from the phage by restriction digestion of purified phage DNA. These cDNA sequences are subcloned into the EcoRI site of the pET vector, pET5c (Novagen; Madison Wis.), which produces T7/Protein 10 fusion proteins that are in-frame with the inserted cDNA. Expression of the recombinant proteins is induced in *E. coli* using IPTG, fractionated by SDS-PAGE and transferred to nitrocellulose filters. The resulting blots are hybridized to the same GST/CD40 fusion protein from the original screening using the hybridization method described above for phage screening. Clones that produce CAP's, which bind the GST/CD40 probe, are sequenced and their amino-acid sequences are deduced. These sequences are checked against nucleotide and protein databases to identify novel or previously described proteins.

New CAP's obtained as described above or CAP's selected from the yeast two hybrid assay are used to produce hybridization probes to screen various tissues by northern blot analysis. Appropriate clones can then be used as hybridization probes to screen commercially-available lambda phage cDNA libraries prepared from an appropriate tissue to obtain a cDNA encoding the entire ORF or to obtain overlapping cDNA sequences which together encode the entire ORF of the various CAP's. In a specific example, the cDNA insert of CAP-1 clone pACT2229 clone was excised with XhoI, $^{32}$P-labeled by a random primer method (see Sambrook et al. supra, 1989), and used to screen a human fetal brain cDNA library in λ-gt11 (Clontech, Inc.; Palo Alto Calif.). Two cDNA clones were obtained having insert sizes of ~2.0 kba (kilobase pair) and 0.1 kba. DNA from the new clones were PCR amplified using primers flanking the cloning site in λ-gt11, and the resulting PCR products were subcloned into a Eco RV-digested, T-tailed pSKII plasmid and their DNA sequence determined by the dideoxynucleotide method. The DNA sequence of the longer of these two clones (pSK-7) extended the coding region of the original cDNAs in the 5'-direction by another 282 amino-acids but the lack of a consensus translation initiation site suggested that the CAP-1 ORF was still incomplete.

A 5'- or 3'-RACE method is useful to obtain cDNA sequence data to complete a full ORF of a partial cDNA clone. The missing 5' ORF of the CAP-1 sequence was obtained using a 5' RACE method to directly amplify the regions of the cDNA from reverse transcribed RNA (Frohman et al., *Proc. Natl. Acad. Sci., USA* 85:8998–9002 (1988), which is incorporated herein by reference). For 5' RACE, 10 μg of total RNA from Raji B-cell lymphoma cells was reverse-transcribed using a specific primer 5'-GCGTTAACTGCTCTGCACAA-3' (SEQ ID NO: 15) and recombinant Moloney murine leukemia virus reverse transcriptase (Gibco/BRL, Inc.; Gaithersburg Md.). The resulting cDNA was subjected to homopolymeric tailing using dCTP and terminal deoxynucleotidyl transferase using a kit from BRL/GIBCO, and then PCR amplified using a universal 5'-forward primer provided by the manufacturer and a 3'-CAP-1-specific reverse primer 5'-GTACATTTTGGACTTGAAGA-3' (SEQ ID NO: 16).

The final PCR product was subcloned into T-tailed pSK-II and a clone (pSK-5') was obtained and the DNA insert sequenced. The insert of pSK-5' provided an additional ~378 bp of DNA sequence to complete the ORF of CAP-1 (see Example III for the complete cDNA sequence of CAP-1).

EXAMPLE III

Characterization of CAP-1

This example describes the characteristics of human CAP-1.

The complete ORF of CAP-1 was obtained by combining the DNA sequence insert present in the original pACT2229 clone insert with the sequence inserts from clones pSK-7 and pSK-5' (see Example I and II for details). The complete CAP-1 ORF encodes a 543 amino-acid protein, having an estimated molecular mass of ~62 kDa (FIG. 1 SEQ ID NO: 2). The full length sequence is based on a predicted translation initiation site that conforms in 6 of 7 positions to the Kozak consensus sequence (Kozak, *J. Biol. Chem.* 266:19867–19870 (1991)). Stop codons were found in all three reading-frames upstream of the longest ORF (nucleotide sequence submitted to Genbank). The absence of a polyadenylation sequence in the 3' untranslated region of the CAP-1 cDNAs (pACT2229 and pSK-7) suggests that the complete 3' end of the CAP-1 cDNA sequence remains to be determined.

A search of the CAP-1 nucleotide sequence against the available databases using the BLAST program 9 (Pearson and Miller, *Meth. Enzymol.* 210: 675–601 (1992), which is incorporated herein by reference) revealed 26% and 30% overall amino-acid sequence homology with TRAF1 and TRAF2, two putative signal transducing proteins that have recently been shown to bind to the cytosolic domain of TNF-R2 (Rothe et al., supra, 1994). The strongest homology was located in the C-terminal regions of these proteins, corresponding to the TRAF domains of TRAF1 and TRAF2 (not shown). The cytosolic domain of CAP-1 is located between residues 384 to 540, and has 57% and 59% amino-acid identity to the analogous domains in TRAF1 and TRAF2, respectively. TRAF1, TRAF2 and CAP-1 are examples of second molecules that contain a TRAF domain and can bind to CAP-1. Due to this high degree of homology, the cytosolic domain of CAP-1 is referred to as a TRAF domain.

Like TRAF2, the CAP-1 protein contains a RING finger domain consensus sequence near its $NH_2$-terminus (residues 53–91). This sequence is believed to form a structure that binds two zinc atoms and is found in several regulatory proteins that can bind to either DNA or RNA, including the DNA repair genes RAD18 of *S. cerevisiae* and UVS-2 of *Neurospora crassa*, the human SS-A/Ro ribonucleoprotein, the Bmi-1, c-dbl, Pml, and RET proto-oncogenes, the recombinase RAG-1, and the human RING-1 protein (reviewed by Freemont, supra, 1993; Schwabe and Klug, supra, 1994; Barlow et al., *J. Mol. Biol.* 237:201–211 (1994)). The RING finger domains of CAP-1 and TRAF2 are 42% identical.

Following the RING finger motif of CAP-1 are three zinc finger-like domains. Two of the domains (ZF2 and ZF3) contain a consensus sequence, which is found in several DNA-binding proteins including the Xenopus transcription factor TFIIIA (Berg, *J. Biol. Chem.* 265:6513–6516 (1990) as well as some RING-finger proteins such as RAD18, and UVS-2 (reviewed by Freemont). The third zinc-finger-like domain (ZF1) is found in CAP-1 (between residues 117–141), but the spacing between the first two cysteines is longer than usual in this case (6 instead of the usual 2 to 4 residues). The TRAF2 protein contains four zinc finger motifs downstream of its RING finger domain. The absence of RING and zinc finger domains in TRAF1 indicates it is more distantly related to the other TRAF family members CAP-1 and TRAF2.

Comparison of the TRAF domain of CAP-1 with those of TRAF1 and TRAF2 suggests that the essential conserved region between these domains can be narrowed to a region of ~150 amino acid residues representing position 385–536 of CAP-1, 254–406 of TRAF1 and 346–497 of TRAF2. The TRAF1 and TRAF2 proteins exhibit additional homology that extends further in the N-terminal direction to include residues 181–406 of TRAF1 and 272–497 of TRAF2 (Rothe et al., supra, 1994). Taken together, these data indicate that CAP-1 is a novel homolog of TRAF2 and a new member of the family of putative signal transducing proteins that contain TRAF-domains.

Although the invention has been described with reference to the examples provided above, it should be understood that various modifications can be made without departing from the spirit of the invention. Accordingly, the invention is limited only by the claims.

We claim:

1. A purified nucleic acid molecule, or the complete complement thereof, comprising a nucleotide sequence encoding a mammalian CD40-Associated Protein (CAP), wherein said protein binds to the cytoplasmic domain of CD40, and wherein said protein comprises a TRAF domain set forth as amino acids 385 to 536 of SEQ ID NO:2.

2. The nucleic acid molecule of claim 1, wherein said mammal is human.

3. A vector, comprising the nucleic acid molecule of claim 1.

4. A host cell, comprising the vector of claim 3.

5. A purified nucleic acid molecule encoding human CD40-Associated Protein-1 (CAP-1), comprising the nucleotide sequence shown in SEQ ID NO:1, or the complete complement thereof.

6. A purified nucleic acid molecule, comprising a nucleotide sequence which encodes the amino acid sequence comprising SEQ ID NO: 2, or the complete complement thereof.

7. A purified nucleic acid molecule, comprising a nucleotide sequence encoding a fragment having a sequence of CD40-Associated Protein (CAP), wherein said fragment binds to the cytoplasmic domain of CD40, and wherein said CAP comprises a TRAF domain set forth as amino acids 385 to 536 of SEQ ID NO:2.

8. The nucleic acid molecule of claim 7, encoding said fragment, comprising the amino acid sequence from positions 384 to 540 shown in SEQ ID NO: 2.

9. The nucleic acid molecule of claim 7, encoding said fragment, comprising the amino acid sequence from positions 384 to 543 shown in SEQ ID NO: 2.

10. The nucleic acid molecule of claim 7, encoding said fragment, comprising the amino acid sequence from positions 363 to 543 shown in SEQ ID NO: 2.

11. The nucleic acid molecule of claim 7, encoding said fragment, comprising the amino acid sequence from positions 82 to 543 shown in SEQ ID NO: 2.

12. The nucleic acid molecule of claim 7, further comprising a nucleotide sequence encoding a RING-finger motif comprising the amino acid sequence from positions 53 to 91 shown in SEQ ID NO:2.

13. The nucleic acid molecule of claim 7, wherein said fragment further comprises zinc finger domains comprising the amino acid sequence from positions 117 to 197 shown in SEQ ID NO:2.

14. The nucleic acid molecule of claim 7, wherein said fragment further comprises a RING-finger motif comprising the amino acid sequence from positions 53 to 91 shown in SEQ ID NO:2 and zinc finger domains comprising the amino acid sequence from positions 117 to 141; positions 148 to 170; and positions 177 to 197 shown in SEQ ID NO:2.

15. A purified nucleic acid molecule encoding a protein that binds to the cytoplasmic domain of mammalian CD40, wherein said protein has a RING-finger motif, zinc finger domains and a TRAF domain, wherein said TRAF domain is encoded by the nucleotide sequence from nucleotide positions 1289 to 1744 shown in SEQ ID NO:1.

16. The nucleic acid molecule of claim 1, wherein said TRAF domain comprises amino acids 384 to 540 of SEQ ID NO:2.

17. The nucleic acid molecule of claim 15, wherein said TRAF domain is encoded by the nucleotide sequence from nucleotide positions 1286 to 1756 shown in SEQ ID NO:1.

18. The nucleic acid of claim 1, wherein said protein does not bind to the cytoplasmic domain of Fas, TNF receptor-1 or TNF receptor-2.

19. The nucleic acid molecule of claim 7, wherein said fragment does not bind to the cytoplasmic domain of Fas, TNF receptor-1 or TNF receptor-2.

* * * * *